(12) United States Patent
Morman et al.

(10) Patent No.: US 6,472,045 B1
(45) Date of Patent: Oct. 29, 2002

(54) LIQUID TRANSFER MATERIAL OF A TRANSVERSELY EXTENSIBLE AND RETRACTABLE NECKED LAMINATE OF NON-ELASTIC SHEET LAYERS

(75) Inventors: Michael Tod Morman, Alpharetta, GA (US); Robert John Schwartz, Cumming, GA (US); Howard Martin Welch, Woodstock, GA (US); Patricia Hsiaoyin Hwang, Alpharetta, GA (US); Thomas Harold Roessler, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/460,467

(22) Filed: Dec. 14, 1999

Related U.S. Application Data

(60) Provisional application No. 60/113,737, filed on Dec. 23, 1998.

(51) Int. Cl.[7] .............................. B32B 3/24; B32B 3/26; B32B 5/04
(52) U.S. Cl. ........................ 428/131; 428/152; 428/141; 428/137; 428/198; 428/219; 428/500; 442/394; 442/400; 442/401; 442/398; 442/328
(58) Field of Search ................................ 428/131, 137, 428/152, 141, 198, 219; 442/394, 400, 401, 398, 328

(56) References Cited

U.S. PATENT DOCUMENTS

| | | | |
|---|---|---|---|
| 3,341,394 A | 9/1967 | Kinney | 161/72 |
| 3,679,538 A | 7/1972 | Druin et al. | 161/159 |
| 3,843,761 A | 10/1974 | Bierenbaum et al. | 264/210 |
| 4,110,392 A | 8/1978 | Yamazaki | 264/127 |
| 4,443,511 A | 4/1984 | Worden et al. | 428/198 |
| 4,457,254 A | 7/1984 | Hungerford | 118/34 |
| 4,596,738 A | 6/1986 | Metcalfe et al. | 428/308.4 |
| 4,640,859 A | 2/1987 | Hansen et al. | 428/105 |
| 4,655,760 A | 4/1987 | Morman et al. | 604/385 A |

(List continued on next page.)

FOREIGN PATENT DOCUMENTS

| | | | |
|---|---|---|---|
| EP | 0 621 985 | 6/1989 | A61F/5/44 |
| EP | 0 419 742 | 4/1991 | B32B/25/08 |
| EP | 0604731 A1 | 7/1994 | |
| EP | 0688263 B1 | 7/1998 | |
| WO | 91/15365 | 10/1991 | B32B/25/08 |
| WO | 93/14928 | 8/1993 | B32B/3/30 |
| WO | 9702133 A | * 1/1997 | |
| WO | 97/02133 | 1/1997 | B32B/3/28 |
| WO | 97/02378 | 1/1997 | D04H/1/54 |
| WO | 98/29239 | 7/1998 | |

*Primary Examiner*—William P. Watkins, III
(74) *Attorney, Agent, or Firm*—Steven D. Flack

(57) ABSTRACT

The present invention is directed to a liquid transfer material formed from a necked laminate and a process for making the laminate. The necked laminate is formed from sheet layers of at least one non-elastic neckable material laminated to at least the film non-elastic film defining a longitudinal and transverse dimension. At least the film layer of the laminate is apertured in an area where liquid transfer through the laminate is desired. The entire laminate may also be apertured. The non-apertured part of the laminate remains extensible and retractable in at least one dimension without significantly reducing the breathability and/or liquid barrier properties of the film layer. This laminate extensibility and retractability is the result of striated rugosities in, for instance, the longitudinal dimension of the film layer which enables the necked laminate to have an amount of extensibility and retractability in the transverse dimension. A breathable laminate may be made by first partially stretching the non-elastic film layer, attaching a non-elastic neckable layer to form a laminate and then stretching the laminate to neck the laminate and lengthen the film to its desired fully stretched configuration.

20 Claims, 17 Drawing Sheets

U.S. PATENT DOCUMENTS

| | | | |
|---|---|---|---|
| 4,663,220 A | | 5/1987 | Wisneski et al. ............ 428/221 |
| 4,720,415 A | | 1/1988 | Vander Wielen et al. ... 428/152 |
| 4,758,239 A | | 7/1988 | Yeo et al. .................... 604/366 |
| 4,789,699 A | | 12/1988 | Kieffer et al. .............. 524/271 |
| 4,833,026 A | | 5/1989 | Kausch .................... 428/315.5 |
| 4,833,172 A | | 5/1989 | Schwarz et al. .............. 521/62 |
| 4,847,134 A | * | 7/1989 | Fahrenkrug et al. ........ 156/163 |
| 4,892,779 A | | 1/1990 | Leatherman et al. ........ 428/220 |
| 4,910,064 A | * | 3/1990 | Sabee ........................ 156/62.4 |
| 4,923,650 A | | 5/1990 | Antoon, Jr. et al. .......... 264/41 |
| 4,965,122 A | | 10/1990 | Morman .................... 428/225 |
| 4,975,469 A | | 12/1990 | Jacoby et al. .............. 521/84.1 |
| 5,114,781 A | | 5/1992 | Morman .................... 428/198 |
| 5,116,662 A | | 5/1992 | Morman .................... 428/198 |
| 5,143,679 A | | 9/1992 | Weber et al. ............. 264/288.8 |
| 5,226,992 A | | 7/1993 | Morman .................... 156/62.4 |
| 5,238,618 A | | 8/1993 | Kinzer ........................ 264/41 |
| 5,244,482 A | | 9/1993 | Hassenboehler et al. ...... 55/528 |
| 5,317,035 A | | 5/1994 | Jacoby et al. ............... 521/143 |
| 5,336,545 A | | 8/1994 | Morman .................... 428/152 |
| 5,385,775 A | | 1/1995 | Wright ...................... 428/284 |
| 5,462,708 A | * | 10/1995 | Swenson et al. ....... 264/174.11 |
| 5,514,470 A | | 5/1996 | Haffner et al. .............. 428/246 |
| 5,536,555 A | * | 7/1996 | Zelazoski et al. ............ 128/849 |
| 5,594,070 A | | 1/1997 | Jacoby et al. ................. 525/88 |
| 5,683,787 A | | 11/1997 | Boich et al. ................ 428/198 |
| 5,695,868 A | | 12/1997 | McCormack ............... 428/283 |
| 5,704,101 A | * | 1/1998 | Majors et al. .............. 156/515 |
| 5,728,085 A | | 3/1998 | Widlund et al. ............ 604/378 |
| 5,763,041 A | | 6/1998 | Leak et al. ................. 428/100 |
| 5,773,374 A | | 6/1998 | Wood et al. ................ 442/328 |
| 5,779,860 A | | 7/1998 | Hollenberg et al. ......... 162/206 |
| 5,789,065 A | | 8/1998 | Haffner et al. .............. 428/152 |
| 5,804,011 A | | 9/1998 | Dutta et al. ................. 156/160 |
| 5,804,241 A | | 9/1998 | Isohata ...................... 426/415 |
| 5,851,937 A | * | 12/1998 | Wu et al. .................... 156/229 |
| 5,885,908 A | * | 3/1999 | Jaeger et al. .................. 442/1 |
| 5,914,084 A | | 6/1999 | Benson et al. .............. 264/284 |
| 5,916,663 A | | 6/1999 | Chappell et al. ............ 428/152 |
| 6,114,263 A | * | 9/2000 | Benson et al. .............. 442/394 |

* cited by examiner

LIQUID TRANSFER MATERIAL OF A TRANSVERSELY EXTENSIBLE AND RETRACTABLE NECKED LAMINATE OF NON-ELASTIC SHEET LAYERS

This application claims priority from U.S. provisional application 60/113,737 filed Dec. 23, 1998.

FIELD OF THE INVENTION

The present invention is directed to a liquid transfer material formed of an apertured, necked laminate for use, for instance, as a liner in a disposable personal care absorbent article and a process for making the laminate. The necked laminate is formed from sheet layers of at least one non-elastic neckable material laminated to at least one non-elastic film layer. The laminate is apertured and is extensible and retractable in at least one dimension. This laminate extensibility and retractability is the result of striated rugosities in, for instance, the longitudinal dimension of the film layer which enables the necked laminate to have an amount of extensibility and retractability in the transverse dimension.

BACKGROUND OF THE INVENTION

Materials that are highly permeable to aqueous liquids are used for top liners, surge layers, and other liquid transfer devices in a wide variety of personal care absorbent articles such as diapers, training pants, incontinence garments, mattress pads, wipers, feminine care products (e.g. sanitary napkins), and in medical applications such as medical drapes, wound dressings and wraps, and the like.

These laminates are made such that the article can be produced with relatively low cost and are thus disposable after only one or a few uses. Much research and development continues, however, to achieve "cloth-like" visual and tactile qualities in these articles without sacrificing breathability and low cost, while also providing an article that generally allows liquid to flow in only one direction. One disadvantage of such articles is that the combination of elements used to make the article does not "give" like, for instance, a fabric made from cotton, which due to its fiber and yarn structure, has a natural ability to extend and retract. These properties are necessary to allow the article to conform to the user'body, thereby feeling and appearing to be more "cloth-like". One known solution to this problem has been to incorporate elastomeric or elastic materials into the article. Unfortunately, incorporation of such materials generally results in increased costs due to more expensive material components. If breathability is attained by stretching a filled film to form micropores, there are problems associated with maintaining breathability of filled elastic films since the recovery of the elastic material after stretching generally closes or partially closes the micropores which had been created for breathability.

Heretofore, to provide laminates with transverse extensibility and retractability, nonwoven web layers were necked (as defined below) prior to applying an elastomeric sheet made using an elastomeric polymer as described in, for instance, commonly assigned U.S. Pat. No. 5,336,545 to Morman. Necking of the nonwoven web allowed it to extend in the transverse direction. Without the elastic sheet attached to the nonwoven web, however, the laminate would not have significant recovery or recovery force after the extension.

The present invention avoids these and other difficulties by providing an inexpensive, liquid transfer material formed from a necked laminate which achieves transverse extensibility and retractability using non-elastic materials.

SUMMARY OF THE INVENTION

The present invention is directed to a liquid transfer material formed from a necked laminate and a process for making the laminate. The necked laminate is formed from sheet layers of at least one non-elastic neckable material laminated to at least the non-elastic film defining a longitudinal and transverse dimension. At least the film layer of the laminate is apertured in an area where liquid transfer through the laminate is desired. The entire laminate may also be apertured. The non-apertured part of the laminate remains extensible and retractable in at least one dimension without significantly reducing the breathability and/or liquid barrier properties of the film layer. This laminate extensibility and retractability is the result of striated rugosities in, for instance, the longitudinal dimension of the film layer which enables the necked laminate to have an amount of extensibility and retractability in the transverse dimension. A breathable laminate may be made by first partially stretching the non-elastic film layer, attaching a non-elastic neckable layer to form a laminate and then stretching the laminate to neck the laminate and lengthen the film to its desired fully stretched configuration.

DETAILED DESCRIPTION OF THE INVENTION

Figure 1:
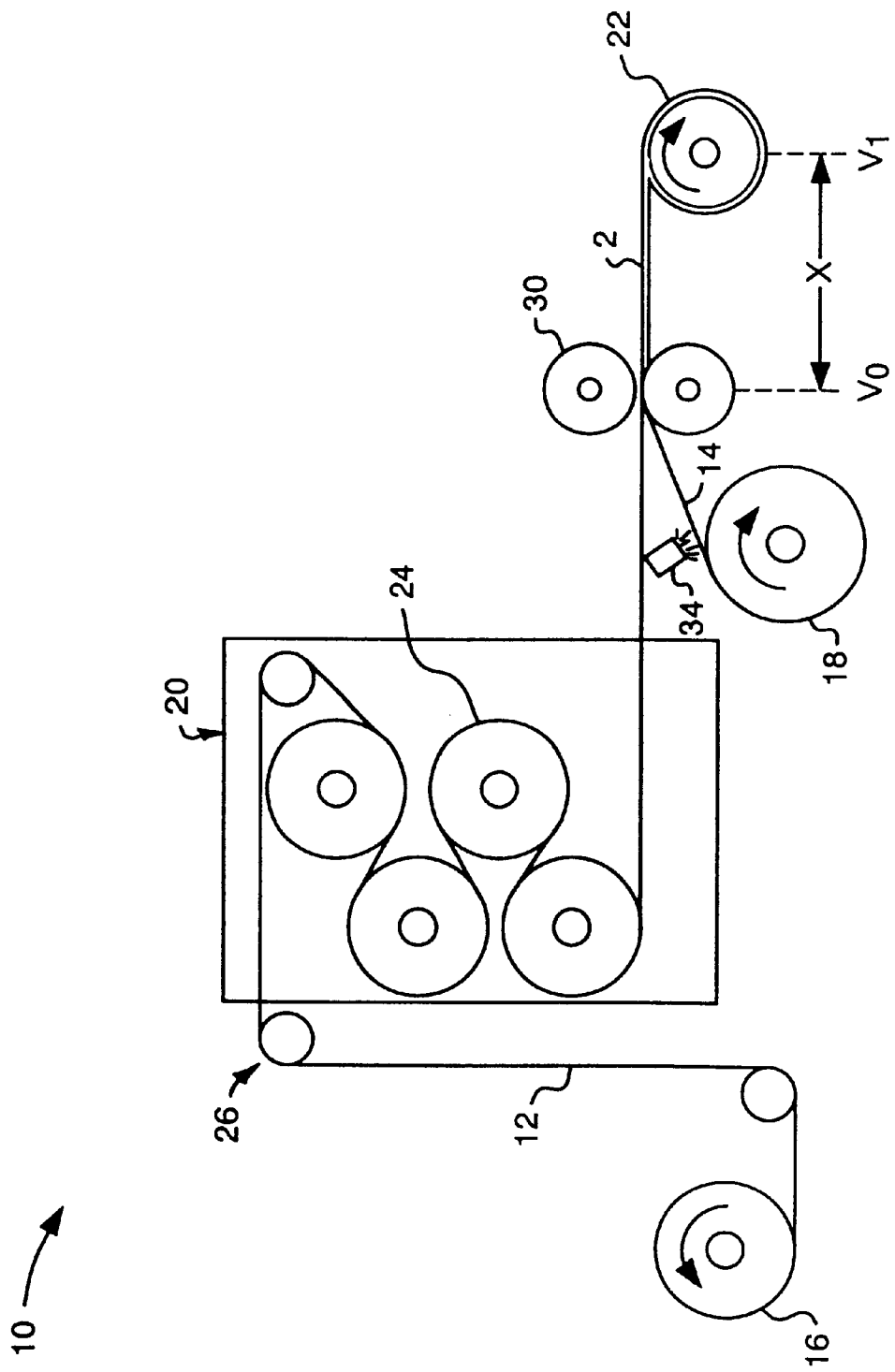
FIG. 1 is a schematic representation of an exemplary process for forming the transversely extensible and retractable necked laminate to form the liquid transfer material of the present invention.

The present invention is directed to a liquid transfer material formed from an apertured necked laminate and a process for making the laminate. The necked laminate is formed from sheet layers of at least one non-elastic neckable material laminated to at least one non-elastic film defining a longitudinal and transverse dimension, wherein the laminate is extensible and retractable in at least one dimension without significantly reducing the breathability and/or liquid barrier properties of the film layer in the non-apertured areas. This laminate extensibility and retractability is the result of striated rugosities in, for instance, the longitudinal dimension of the film layer which enable the necked laminate to have an amount of extensibility and retractability in the transverse dimension.

The term "liquid transfer material" refers to a material present in at least two layers, such as a layer of a fibrous nonwoven web and a layer of apertured film, which has an open or porous structure, and which is water permeable permitting the flow of water and other aqueous liquids through the apertures. For a nonwoven web to be a liquid transfer material: (1) the spaces between its fibers or filaments must be large enough and frequent enough to permit flow of liquid through the web; or (2) a surfactant may be necessary; or (3) the nonwoven may also be perforated. For a film to be a liquid transfer material, it must have apertures, slits or other openings large enough and frequent enough to permit flow of liquid through the film.

The necked laminate is made, for example, by first partially stretching the non-elastic film layer, attaching a non-elastic neckable layer to the film layer to form a laminate, and then stretching the laminate to neck the laminate and to complete the stretching/orientation of the film layer to its desired fully stretched configuration. When a laminate is "fully stretched" it exhibits completely sufficient for the intended use, for example, breathability and tensile strength. As used herein, the term "partially stretched" means that the film and/or laminate is not fully stretched.

As used herein, the term "neck" or "neck stretch" interchangeably means that the laminate is drawn such that it is extended under conditions reducing its width or its transverse dimension by drawing and elongating to increase the length of the fabric. The controlled drawing may take place under cool temperatures, room temperature or greater temperatures and is limited to an increase in overall dimension in the direction being drawn up to the elongation required to break the laminate, which in most cases is about 1.2 to 1.6 times. The laminate can then be heated to impart a heat set to the necked laminate. When relaxed, the laminate does not retract toward its original longitudinal dimension or extend to its original transverse dimension, but instead essentially maintains its necked dimension. The necking process typically involves unwinding a sheet from a supply roll and passing it through a brake nip roll assembly driven at a given linear speed. A take-up roll or nip, operating at a linear speed higher than the brake nip roll, draws the fabric and generates the tension needed to elongate and neck the fabric. U.S. Pat. No. 4,965,122 issued to Morman, and commonly assigned to the assignee of the present invention, discloses a reversibly necked nonwoven unlaminated material which may be formed by necking the material, then heating the necked material, followed by cooling and is incorporated herein by reference in its entirety. The heating of the necked material causes additional crystallization of the polymer giving it a heat set.

As used herein, the term "neckable material or layer" means any material which can be necked such as a nonwoven, woven, or knitted material. As used herein, the term "necked material" refers to any material which has been drawn in at least one dimension, (e.g. lengthwise), reducing the opposite dimension, (e.g. width), such that when the drawing force is removed, the material can be pulled back to its original width. The necked material has a higher basis weight per unit area than the un-necked material. When the necked material is pulled back to its original un-necked width, it should have about the same basis weight as the un-necked material. This differs from stretching/orienting the film layer, during which the film is thinned and the basis weight is reduced.

The term "laminate" as used herein means a combination made up of at least two sheet layers wherein at least one sheet layer is a film layer and at least one sheet layer is a layer of neckable material. Also, the term "longitudinal direction" or "LD" means the length of a material in the direction in which the material is moving when it is produced. The "longitudinal dimension" therefore, is the dimension of the longitudinal direction. The term "transverse direction" or "TD" means the width of the material, i.e. a direction generally perpendicular to the longitudinal direction. Likewise, the "transverse dimension" therefore, is the dimension of the transverse direction.

Referring to FIG. 1, there is schematically illustrated an exemplary process 10 for forming the transversely extensible and retractable necked laminate 2, that, once apertured, forms the liquid transfer material of the present invention. For all of the figures, like reference numerals represent the same or equivalent structure or element. A non-elastic film layer 12 is unwound from a first supply roll 16 and fed into a stretching means 20 using guide rollers 26. Once in the stretching means 20, the non-elastic film layer 12 is partially stretched in a longitudinal direction by stretching rollers 24 which stretch and thin the film layer 12. Such stretching usually occurs with little or no necking of the film layer. If the distance between the rolls is too large, irreversible narrowing of the film layer can occur. After partially stretching the film layer 12 and prior to laminating to the neckable material 14, the tension of the film layer 12 is only that which is sufficient to keep the layer from sagging or retracting. In other words, it is not necessary to continue stretching the film layer 12 between the stretching means 20 and laminating means 30.

A non-elastic neckable material 14 likewise is unwound from second supply roll 18 which rotates in the direction of the arrows associated therewith. In an embodiment where partial film stretching is controlled to avoid film necking, matching the film width to the width of the neckable material is facilitated. It should be understood that the non-elastic neckable material and/or film layer may just as well be formed in-line rather than being pre-made and unwound. Adhesive sprayer 34 applies adhesive to the surface of the neckable material 14 which is then laminated to the film layer 12 using laminating means 30 (e.g. nip rolls). The laminate could also be formed by thermal point bonding, sonic welding, point bonding, or the like.

Figure 3:
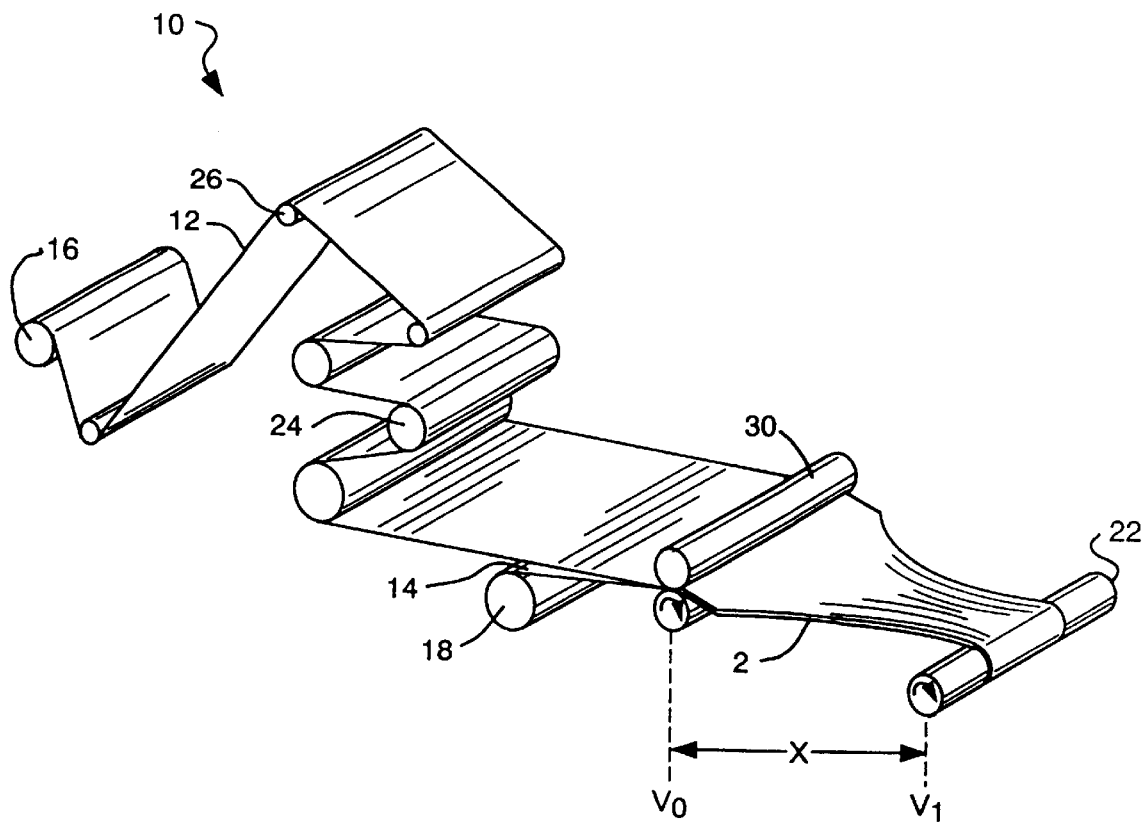
FIG. 3 is a perspective view of the process of FIG. 1 showing the stretching of the non-elastic film layer, attachment of the non-elastic neckable material and the necking of the laminate.

The thus formed laminate 2 is then necked by a necking means 22 (e.g. take-up roll) which may be accomplished as shown in FIG. 1 wherein the surface speed $V_0$ of laminating means 30 is less than the surface speed $V_1$ of necking means 22. As used herein, to say that the laminate has been drawn 1X means that surface speed $V_0$ is equal to surface speed $V_1$. The "necking draw", therefore, is the surface speed $V_1$ divided by surface speed $V_0$. Further, the distance x between laminating means 30 and necking means 22, must be sufficient to allow for necking of the laminate, such that the transverse dimension of the laminate is less than that of the un-necked laminate. As a general rule, the distance x should be at least two times the transverse dimension (width) of the laminate. Such necking provides striated rugosities in the film and/or laminate resulting in transverse extensibility and retractability to the necked laminate 2 and more "cloth-like" aesthetics (e.g. the necked laminate is softer than prior art laminates and looks more like a woven material because of the striated rugosities). FIG. 3 is essentially the same as FIG. 1 except that it is a perspective view showing the necking of the laminate.

Figure 5:
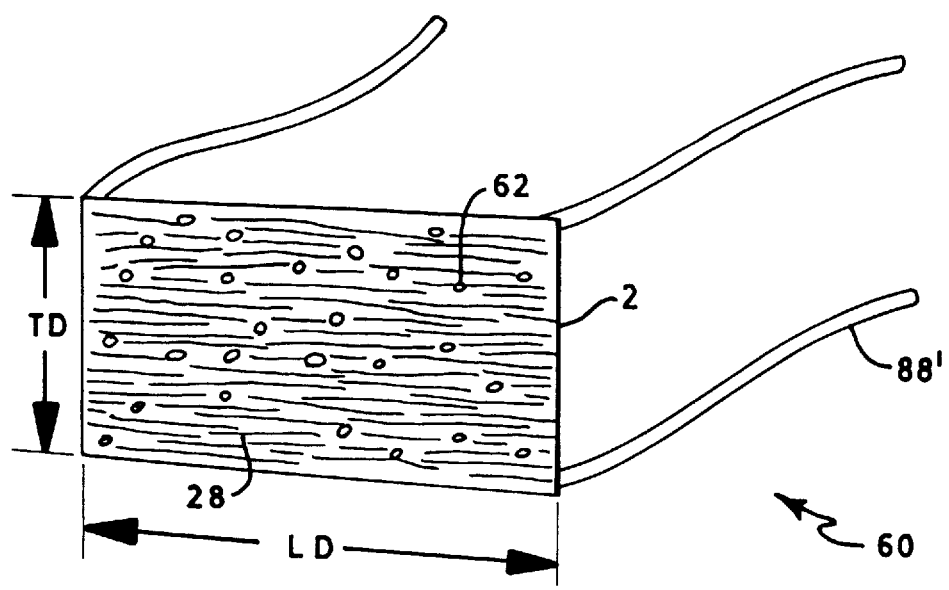
FIG. 5 is a plan view of an exemplary medical article, in this case, a facemask, which may utilize the liquid transfer material of the present invention.
Figure 17:
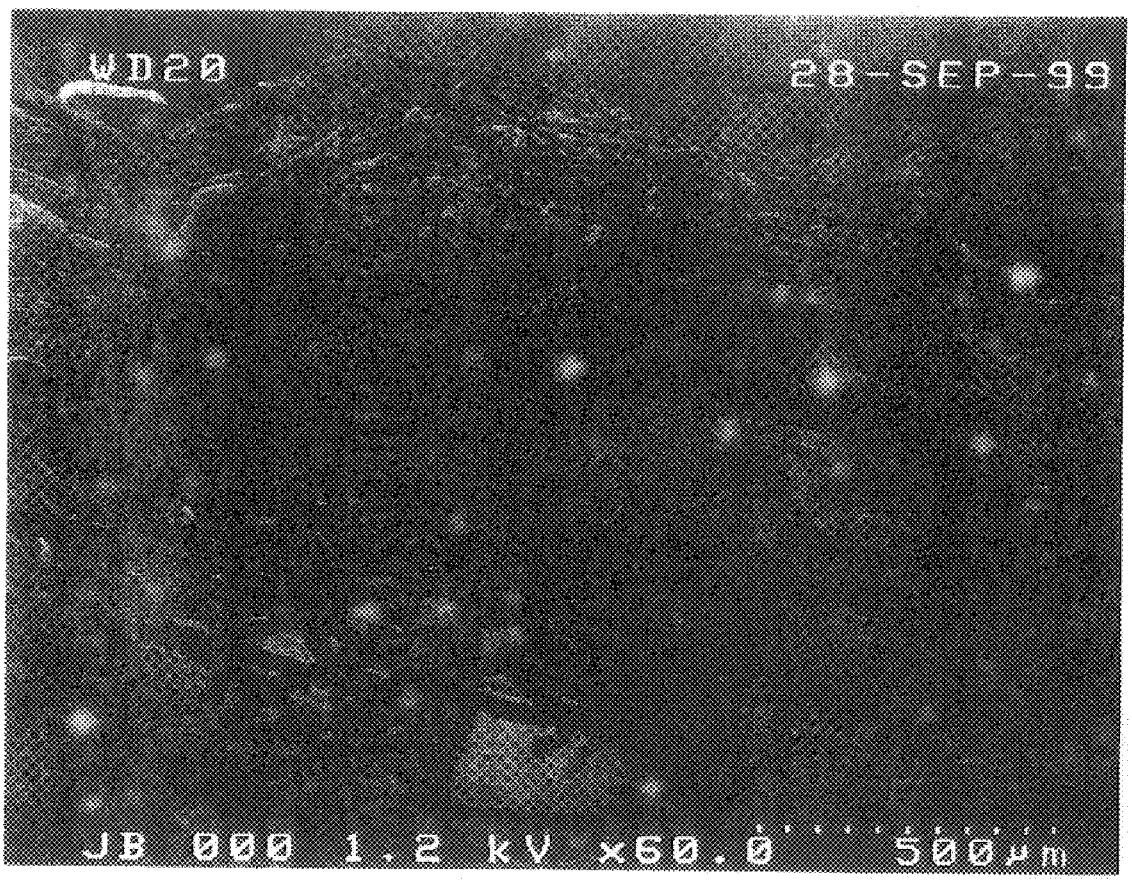
FIG. 17 is a an oblique view of an optical photomicrograph of the apertured liquid transfer material, including a layer of bonded carded web, wherein the apertures have not adversely impacted the striated rugosities.

The laminate 2 is then further processed, (not shown) to form openings, such as apertures 62 (as shown in FIGS. 5 and 17), to create the liquid transfer material of the present invention. The openings can be in the form of apertures 62 (as shown), slits (not shown), or any other form as long as the openings are of sufficient size, and density or frequency, to readily facilitate liquid transfer through the material. As used herein, the term "apertures" is used to generically describe this type of opening. The apertures may be in any form including holes and slits and may be formed by processes generally known. It will be understood by one of ordinary skill in the art, that an individual layer of the laminate, or the entire laminate, may be apertured as necessary to result in a laminate that allows liquid to transfer through the material to the extent appropriate to the intended use. Examples of exemplary processes for forming exemplary apertures may be found in commonly assigned U.S. Pat. No. 5,704,101 to Majors et al. and U.S. Pat. No. 5,925,026 to Arteman et al., which are incorporated herein by reference in their entirety.

Figure 2:
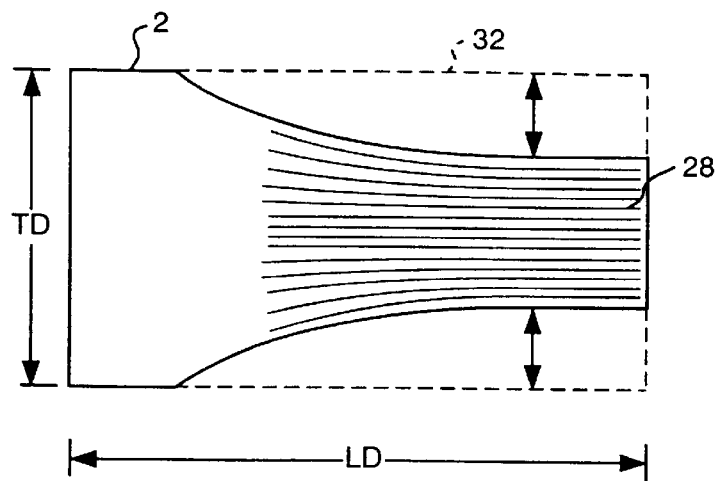
FIG. 2 is a top plan view of the laminate as it is being necked showing the striated rugosities in the longitudinal dimension.
Figure 6:
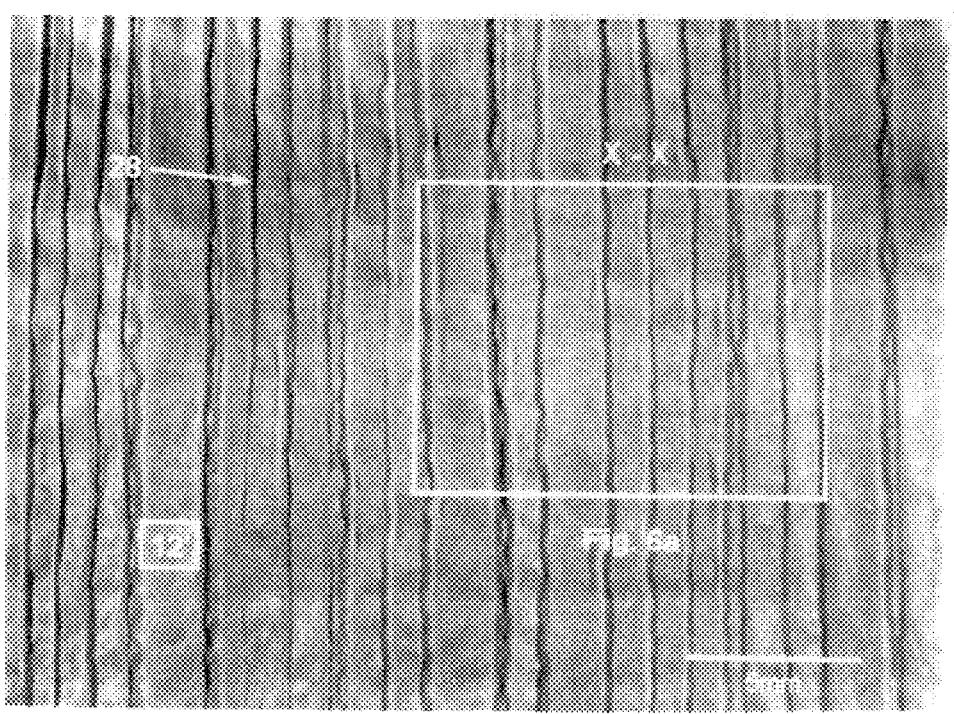
FIG. 6 is a top plan view of an optical photomicrograph (High Resolution Digital Image) of the non-elastic film layer side of a laminate to form the liquid transfer material of the present invention showing the striated rugosities.
Figure 6A:
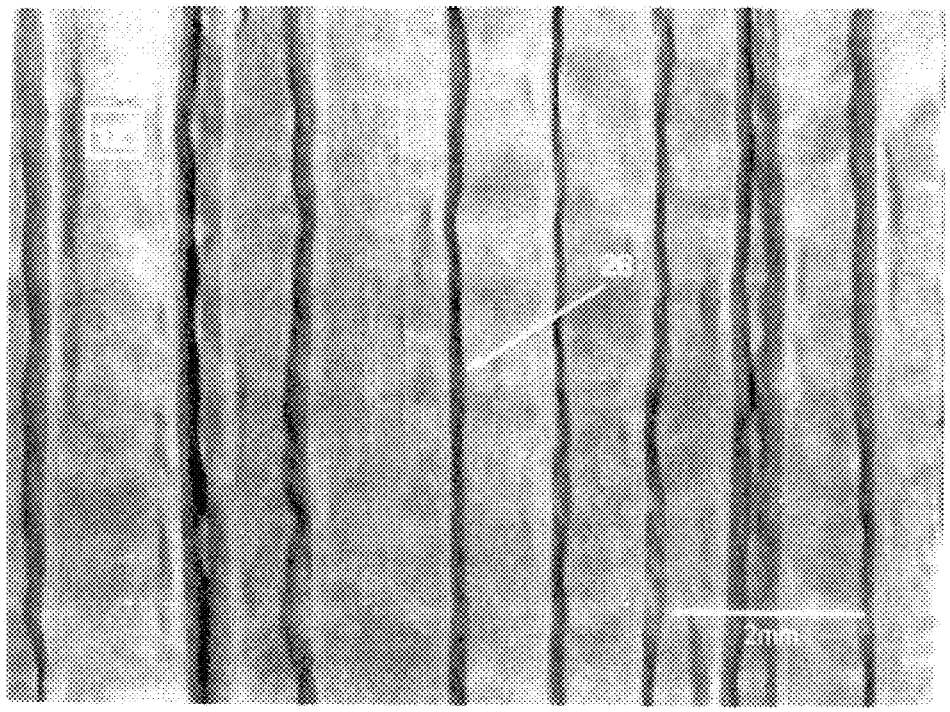
FIG. 6a is a top plan view of an optical photomicrograph of the enlarged section of FIG. 6 showing the variation and randomness of the striated rugosities.
Figure 7:
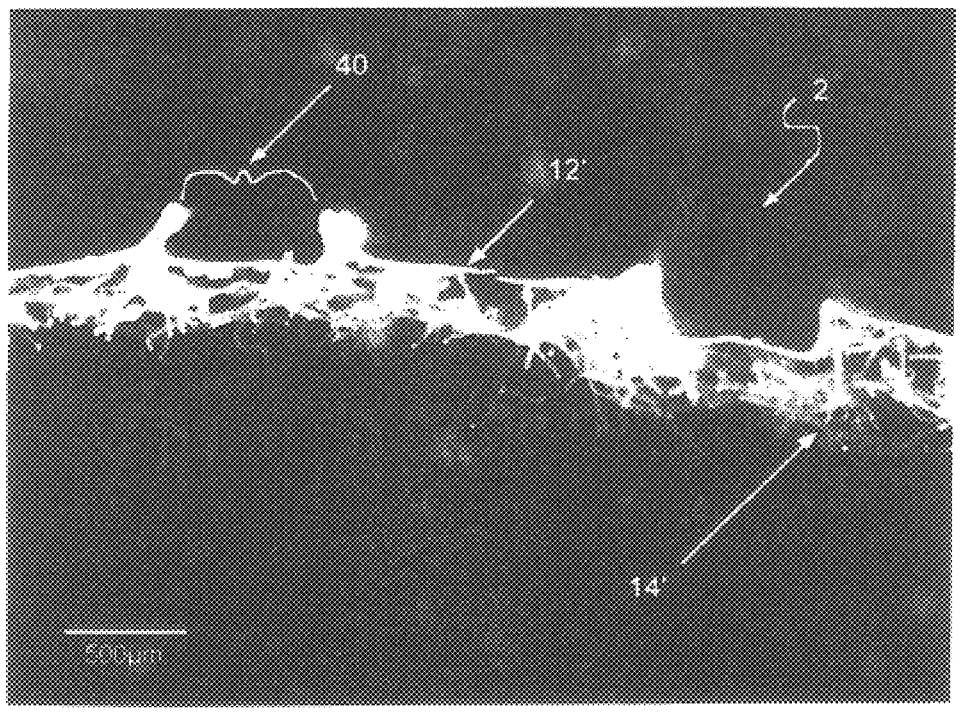
FIGS. 7, 8, and 9 are cross-sectional optical photomicrographs of the laminates useful in the liquid transfer material of the present invention showing trapezoidal, pleated, and crenellated striations, respectively.
Figure 8:
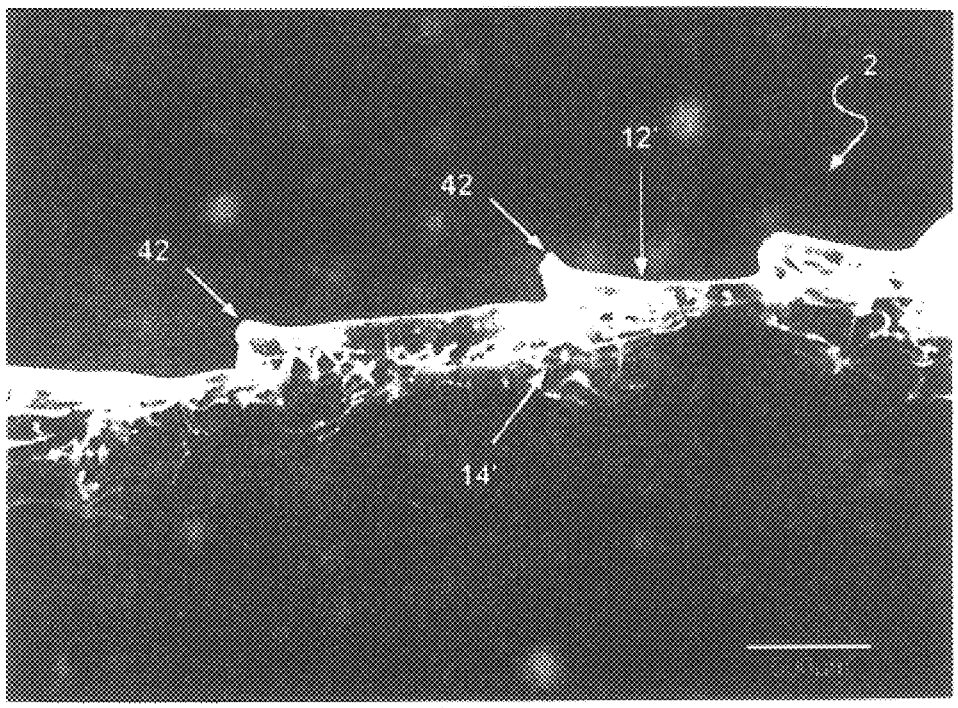
Figure 9:
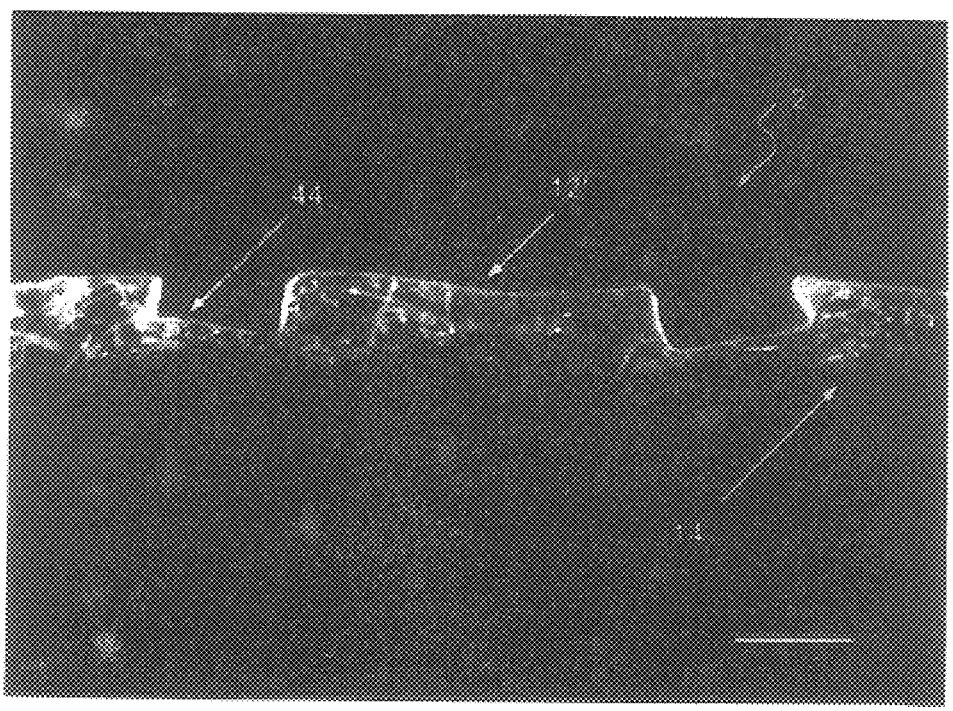

It is known that stretching and orienting a filled film layer causes micropores to form in the film, but longitudinal striated rugosities do not typically form in the film layer when stretched. The film layer would instead become physically thinner and may narrow slightly. Further, to then attempt to elongate the oriented filled film layer in the TD could result in tearing when very little force is applied, which is likely due to tearing along the LD microslits which have formed from stretching and orienting the filled film layer. The polymer used to make the film, the amount of filler, and how much the film was totally drawn affects how much the film can be TD extended before it splits. By necking the laminate, the non-elastic neckable material, which is attached to the non-elastic film layer, will neck and bring the non-elastic film layer with it, thereby forming the longitudinal striated rugosities in the film which allow the film layer to extend and retract in the TD without adversely affecting the breathability, barrier properties, and/or integrity of the film. In FIG. 2, the striated rugosities 28 are shown figuratively in the longitudinal direction LD of laminate 2 which has been necked in the transverse direction TD. The un-necked transverse dimension 32 is the dimension the laminate would have but for the necking. The double edged arrows indicate the extensibility and retractability of the laminate in the TD. As used herein, the term "striated rugosities", refers to thin, narrow grooved, or channeled wrinkles in the non-elastic film layer 12 of necked laminate. Referring to FIG. 6, the striated rugosities can be shown generally at 28 in the surface of film layer 12' of sample 6 (in the Examples below). FIG. 6a is an enlarged view of FIG. 6. As can be seen in these figures, the striated rugosities have a variable and random pattern. FIGS. 7–9 are enlarged cross-sectional end views of the laminate 2 of FIG. 6 at different points along the section showing the variable striations in film layer 12' which is attached to neckable material 14'. FIG. 7 generally shows a trapezoidal striation 40; FIG. 8 generally shows pleats 42; while FIG. 9 generally shows crenellated striations 44. As used herein, the term "crenellated" is used as in crenellated molding which, according to Webster'Third New International Dictionary, unabridged, copyright 1986, is "a molding of . . . [an] indented pattern common in medieval buildings". The striated rugosities actually occur predominantly in the non-elastic film layer, but can be seen through the necked material and give the entire laminate a more cloth-like appearance. If one were to delaminate the film layer from the neckable material after necking, the film layer would visually retain the striated rugosities while the neckable material would not. A theory that may be ascribed to this phenomena is that the film actually crystallizes when being drawn and forming the striated rugosities, thereby setting a "memory" into the film which works to retract the laminate once it has been extended.

By the term "non-elastic", what is meant is that the sheet layers are made from polymers that are generally considered to be inelastic. In other words, use of such inelastic polymers to form the sheet layers would result in sheet layers which are not elastic. As used herein, the term "elastic" means any material which, upon application of a biasing force, is stretchable, that is, elongatable, at least about 60 percent (i.e., to a stretched, biased length which is at least about 160 percent of its relaxed unbiased length), and which will immediately recover at least 55 percent of its elongation upon release of the stretching, elongating force. By "immediately" what is meant is that the elastic material will behave, for instance, as a rubber band to recover as soon as the elongating force is removed. A hypothetical example would be a one (1) inch sample of a material which is elongatable to at least 1.60 inches (4.06 cm) and which, upon being elongated to 1.60 inches (4.06 cm) and released, will immediately, i.e. within less than one second, recover to a length of not more than 1.27 inches (3.23 cm). Many elastic materials may be elongated by much more than 60 percent, for example, 100 percent or more, and many of these will recover to substantially their initial relaxed length, for example, to within 105 percent of their initial relaxed length upon release of the stretching force.

The terms "extensible and retractable" have been chosen to describe what the laminate made of non-elastic sheet layers does upon application and removal of a biasing force. Those having skill in the art of elastic materials have conventionally used the phraseology "stretch and recover" to describe what an elastic material does upon application and removal of a biasing force as described above.

For purposes of the present invention, wherein the materials used to form the sheet layers are not elastic, the terminology chosen to describe the phenomena exhibited by the laminate upon application and removal of a biasing force is "extensible and retractable". The liquid transfer materials of the present invention do not stretch as far as that of a highly elastic material, which can stretch in excess of 500%. In fact, the film layer does not actually stretch; instead, the striated rugosities are essentially temporarily removed when a biasing force is applied in the transverse direction. If these striated rugosities are not permanently removed by, for instance, overextending the laminate in the transverse dimension, or heating the extended laminate to impart a "new" "memory", the material will eventually retract to close to its original dimension. Such a property has heretofore been unknown in laminates made solely from non-elastic neckable and film materials.

As used herein, the term "polymer" generally includes, but is not limited to, homopolymers, copolymers, for example, block, graft, random and alternating copolymers, terpolymers, etc. and blends and modifications thereof. Such blends include blends of inelastic polymers with elastic polymers as long as the elastic polymers are used in such a quantity and composition that the use of these would not render the polymer elastic. Unless otherwise specifically limited, the term "polymer" shall include all possible geometrical configurations of the molecule. These configurations include, but are not limited to, isotactic, syndiotactic and random symmetries.

The non-elastic film layer 12 can be made from either cast or blown film equipment, can be coextruded and can be embossed if so desired. The film layer may be made from any suitable non-elastic polymer composition.

Such polymers include but are not limited to non-elastic extrudable polymers such as polyolefin or a blend of polyolefins, nylon, polyesters, and ethylene vinyl alcohol. More particularly, useful polyolefins include polypropylene and polyethylene. Other useful polymers include those described in U.S. Pat. No. 4,777,073 to Sheth, assigned to Exxon Chemical Patents Inc., such as a copolymer of polypropylene and low density polyethylene or linear low density polyethylene.

Other useful polymers include those referred to as single site catalyzed polymers such as "metallocene" polymers produced according to a metallocene process and which have limited elastic properties. The term "metallocene-catalyzed polymers" as used herein includes those polymer materials that are produced by the polymerization of at least ethylene using metallocenes or constrained geometry catalysts, a class of organometallic complexes, as catalysts. For example, a common metallocene is ferrocene, a complex of a metal between two cyclopentadienyl (Cp) ligands. Metallocene process catalysts include bis(n-butylcyclopentadienyl)titanium dichloride, bis(n-butylcyclopentadienyl)zirconium dichloride, bis (cyclopentadienyl)scandium chloride, bis(indenyl) zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl (cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to the Dow Chemical Company. Such compounds are also discussed in U.S. Pat. 5,064,802 to Stevens et al. and also assigned to Dow.

Such metallocene polymers are available from Exxon Chemical Company of Baytown, Texas under the trade name EXXPOL® for polypropylene based polymers and EXACT® for polyethylene based polymers. Dow Chemical Company of Midland, Michigan has polymers commercially available under the name ENGAGE®. Preferably, the metallocene polymers are selected from copolymers of ethylene and 1-butene, copolymers of ethylene and 1-hexene, copolymers of ethylene and 1-octene and combinations thereof. For a more detailed description of the metallocene polymers and the process for producing same which are useful in the present invention, see commonly assigned U.S. patent application Ser. No. 774,852 abandoned and Ser. No. 854,658 abandoned first filed on 27. Dec. 27, 1996 in the names of Gwaltney et al., which is incorporated herein by reference in its entirety. In general, the metallocene-derived ethylene-based polymers of the present invention have a density of at least 0.900 g/cc.

The non-elastic film layer may be a multi-layered film layer which may include a core layer, or "B" layer, and one or more skin layers, or "A" layers, on either side or both sides of the core layer. When more than one skin layer is present, is not a requirement that the skin layers be the same. For instance, there may be an A layer and an A' layer. Any of the polymers discussed above are suitable for use as a core layer of a multi-layered film. Any of the fillers disclosed herein are suitable for use in any film layer.

The skin layer will typically include extrudable thermoplastic polymers and/or additives which provide specialized properties to the non-elastic film layer. Thus, the skin layer may be made from polymers which provide such properties as antimicrobial, barrier, water vapor transmission, adhesion and/or antiblocking properties. The polymers are thus chosen for the particular attributes desired. Examples of possible polymers that may be used alone or in combination include homopolymers, copolymers and blends of polyolefins as well as ethylene vinyl acetate (EVA), ethylene ethyl acrylate (EEA), ethylene acrylic acid (EAA), ethylene methyl acrylate (EMA), ethylene butyl acrylate (EBA), polyester (PET), nylon (PA), ethylene vinyl alcohol (EVOH), polystyrene (PS), polyurethane (PU), and olefinic thermoplastic elastomers which are multistep reactor products wherein an amorphous ethylene propylene random copolymer is molecularly dispersed in a predominately semicrystalline high polypropylene monomer/low ethylene monomer continuous matrix. The skin layer can be formed of any semicrystalline or amorphous polymer, including one that is elastic. However, the skin layer is generally a polyolefin such as polyethylene, polypropylene, polybutylene or a ethylene-propylene copolymer, but may also be wholly or partly polyamide such as nylon, polyester such as polyethylene terephthalate, polyvinylidene fluoride, polyacrylate such as poly(methyl methacrylate)(only in blends) and the like, and blends thereof.

The non-elastic film layers of the present invention can be made from breathable or non-breathable materials and will be apertured either prior to lamination to the neckable material or after lamination. The non-elastic film layer may contain such fillers as micropore developing fillers, e.g. calcium carbonate; opacifying agents, e.g. titanium dioxide; and antiblock additives, e.g. diatomaceous earth.

Fillers may be incorporated for developing micropores during orientation of the non-elastic film layer resulting in breathable films. Once the particle-filled film has been formed, it is then either stretched or crushed to create pathways through the film layer. Generally, to qualify as being "breathable" for the present invention, the resultant laminate, prior to aperturing, should have a water vapor transmission rate (WVTR) of at least about 250 g/m$^2$/24 hours as may be measured by a test method as described below. Preferably, the laminate will have a WVTR of at least about 1000 g/m$^2$/24 hours.

As used herein, a "micropore developing filler" is meant to include particulates and other forms of materials which can be added to the polymer and which will not chemically interfere with or adversely affect the extruded film but are able to be uniformly dispersed throughout the film layer. Generally, the micropore developing fillers will be in particulate form and usually will have somewhat of a spherical shape with average particle sizes in the range of about 0.5 to about 8 microns. The non-elastic film layer will usually contain at least about 20 volume percent, preferably about 20 to about 45 volume percent, of micropore developing filler based upon the total volume of the film layer. Both organic and inorganic micropore developing fillers are contemplated to be within the scope of the present invention provided that they do not interfere with the film formation process, the breathability of the resultant non-elastic film layer, the liquid barrier properties of the film layer or its ability to bond to another sheet layer.

Examples of micropore developing fillers include calcium carbonate ($CaCO_3$), various kinds of clay, silica ($SiO_2$), alumina, barium sulfate, sodium carbonate, talc, magnesium sulfate, titanium dioxide, zeolites, aluminum sulfate, cellulose-type powders, diatomaceous earth, magnesium sulfate, magnesium carbonate, barium carbonate, kaolin, mica, carbon, calcium oxide, magnesium oxide, aluminum hydroxide, pulp powder, wood powder, cellulose derivative, polymer particles, chitin and chitin derivatives. The micropore developing filler particles may optionally be coated with a fatty acid, such as stearic acid, or a larger chain fatty acid such as behenic acid, which may facilitate the free flow of the particles (in bulk) and their ease of dispersion into the polymer matrix. Silica-containing fillers may also be present in an effective amount to provide antiblocking properties.

The non-elastic neckable material of the present invention is air-permeable. Such non-elastic neckable materials include nonwoven webs, woven materials and knitted materials. As used herein, the term "nonwoven fabric or web" means a web having a structure of individual fibers or threads which are interlaid, but not in an identifiable manner as in a knitted fabric. Nonwoven fabrics or webs have been formed from many processes, for example, bonded carded web processes, meltblowing processes and spunbonding processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91). The non-elastic neckable material of the present invention has a basis weight of 5 to 90 gsm, preferably 10 to 90 gsm, more preferably 20 to 60 gsm.

The non-elastic neckable material is preferably formed from at least one member selected from fibers and/or filaments of inelastic polymers. Such polymers include polyesters, for example, polyethylene terephthalate, polyolefins, for example, polyethylene and polypropylene, polyamides, for example, nylon 6 and nylon 66. These fibers or filaments are used alone or in a mixture of two or more thereof.

Suitable fibers for forming the neckable material 14 include natural and synthetic fibers as well as bicomponent, multi-component, and shaped polymer fibers. A plurality of neckable materials may also be used according to the present invention. Examples of such materials can include, for example, spunbond/meltblown composites and spunbond/meltblown/spunbond composites such as are taught in Brock et al., U.S. Pat. No. 4,041,203 which is incorporated herein by reference in its entirety. Neckable materials may also be formed from composites such as "coform" as described in commonly assigned U.S. Pat. No. 4,100,324 to Anderson et al.

As used herein, the term "spunbonded fibers" refers to small diameter fibers which are formed by extruding through one or more extruders attached to one or more banks made up of at least transfer piping and spinplates to produce molten thermoplastic material as filaments from a plurality of fine, usually circular, capillaries in a spinneret with the diameter of the extruded filaments then being rapidly reduced as by, for example, in Appel et al., U.S. Pat. No. 4,340,563; Matsuki, et al., U.S. Pat. No. 3,802,817; Dorschner et al., U.S. Pat. No. 3,692,618; Kinney, U.S. Pat. Nos. 3,338,992 and 3,341,394; Hartman, U.S. Pat. No. 3,502,763; and Dobo et al., U.S. Pat. No. 3,542,615. Spunbond fibers are generally not tacky when they are deposited onto a collecting surface. Spunbond fibers are generally continuous and have average diameters (from a sample of at least 10) larger than 7 microns, more frequently, between about 10 and 40 microns. The resulting matt of fibers is then bonded to form a strong neckable fabric. This bonding may be performed by ultrasonic bonding, chemical bonding, adhesive bonding, thermal bonding, needle punching, hydroentangling and the like.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, and are generally smaller than 20 microns in average diameter.

As used herein the term "microfibers" means small diameter fibers having an average diameter not greater than about 75 microns, for example, having an average diameter of from about 0.5 microns to about 50 microns, more particularly, about 2 microns to about 40 microns. Another frequently used expression of fiber diameter is denier, which is defined as grams per 9000 meters of a fiber and may be calculated as fiber diameter (in microns) squared, multiplied by the polymer density in grams/cc, multiplied by 0.00707. For fibers made from the same polymer, a lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex", which is defined as the grams per kilometer of fiber. Tex may be calculated as denier/9.

Formation of a "bonded carded web" may be made using a number of known processes such as conventional carding equipment, for example. Preferred are those methods which result in a generally uniform blend of the fibers and produce a low density, bulky batt or web. Other examples include carding, picking and doffing apparatus as well as airlaying apparatus. In general, such equipment separates the fibers and redistributes them in an air stream with turbulent mixing and deposition on a collecting surface. Examples of such processes and apparatus can be found, for example in commonly assigned U.S. Pat. No. 4,548,856 to Ali Khan et al.

Many polyolefins are available for fiber production according to the present invention, for example, fiber forming polypropylenes include Exxon Chemical Company's ESCORENE PD 3445 polypropylene and Himont Chemical Company's PF-304. Polyethylenes such as Dow Chemical's ASPUN 6811A linear low density polyethylene, 2553 LLDPE and 25355 and 12350 high density polyethylene are also suitable polymers. The polyethylenes have melt flow rates of about 26, 40, 25 and 12, respectively. Many other polyolefins are commercially available.

The nonwoven web layer may be bonded to impart a discrete bond pattern with a prescribed bond area. This is known as thermal point bonding. "Thermal point bonding" involves passing a web of fibers to be bonded between a heated calender or patterned roll and an anvil roll. The calender roll is patterned so that the entire neckable material is not bonded across its entire surface. In fact, this feature is very important for necking of neckable materials as described herein. If too much bond area is present on the neckable material, it will break before it necks. If there is not enough bond area, then the neckable material will pull apart. Typically, the percent bonding area useful in the present invention ranges from around 5% to around 40% of the area of the neckable material. Many patterns for calender rolls have been developed. As will be understood by those skilled in the art, bond area percentages are, of necessity, described in approximations or ranges since bond pins are normally tapered and wear down over time. As those skilled in the art will also recognize, references to "pins/in.$^2$" and "bonds/in.$^2$" are somewhat interchangeable since the pins will create bonds in the substrate in essentially the same sizes and surface relationship as the pins on the roll. There are a number of discrete bond patterns which may be used. See, for example, Brock et al., U.S. Pat. No. 4,041,203. One example of a pattern has points and is the Hansen Pennings or "H&P" pattern with about 200 bonds/square inch as taught in U.S. Pat. No. 3,855,046 to Hansen and Pennings. The H&P pattern has square point or pin bonding areas wherein each pin may have a side dimension of 0.038 inches (0.965 mm), for example, resulting in a pattern having a bonded area of about 30%. Another typical point bonding pattern is the expanded Hansen and Pennings or "EHP" bond pattern which produces a bond area of about 15% to 18% which may have a square pin having a side dimension of 0.037 inches (0.94 mm), for example, and a pin density of about 100 pins/in$^2$. Another typical point bonding pattern designated "714") has square pin bonding areas wherein each pin may have a side dimension of 0.023 inches, for example, for a bond area of 15% to 20% and about 270 pins/in$^2$. Other common patterns include a "Ramisch" diamond pattern with repeating diamonds having a bond area of 8% to 14% and 52 pins/in.$^2$, a HDD pattern, which comprises point bonds having about 460 pins/in.$^2$ for a bond area of about 15% to about 23%, as well as a wire weave pattern looking as the name suggests, e.g. like a window screen and having a bond area of 15% to 20% and 302 bonds/in.$^2$. Another bond pattern for a spunbond facing web is a "S" weave pattern as described in commonly assigned U.S. Pat. No. 5,964,742 to McCormack et al. which is incorporated herein by reference in its entirety.

Laminating the film layer to the neckable material to form the laminate may occur by typical methods known in the art including adhesive bonding, point bonding, thermal point bonding, and sonic welding. The use of inelastic and/or elastic adhesives for the adhesive bonding is contemplated herein. As discussed in more detail below, the use of an elastic adhesive has not been found to appreciably impact ease of extensibility. When the film layer and neckable material are bonded through the use of heat and/or pressure, laminating means 30 (FIG. 1) such as laminating rollers may be used. The laminating rollers may be heated and point bonding may be used. The temperature at which the laminating rollers are heated depends on the properties of the film and/or neckable material but is usually in the range of 200–275° F. (93–135° C.).

Also contemplated by the present invention is the attachment of a second neckable material, which may be simply unwound and laminated to the partially stretched film, or the partially necked laminate as described above or formed directly in-line of the process. Such three layer laminates are particularly useful in medical and industrial protective garment applications. Similarly, other film layers or partially stretched film layers may be combined. Turning to FIG. 17, an exemplary article, in this case a three layer structure of the film layer, spunbond layer and a bonded carded web, (as described in more detail below in Example 3), is shown. The Figure is an oblique view of an optical photomicrograph of a three-layered liquid transfer material, wherein the apertures have not adversely impacted the striated rugosities found in the film layer.

Figure 4:
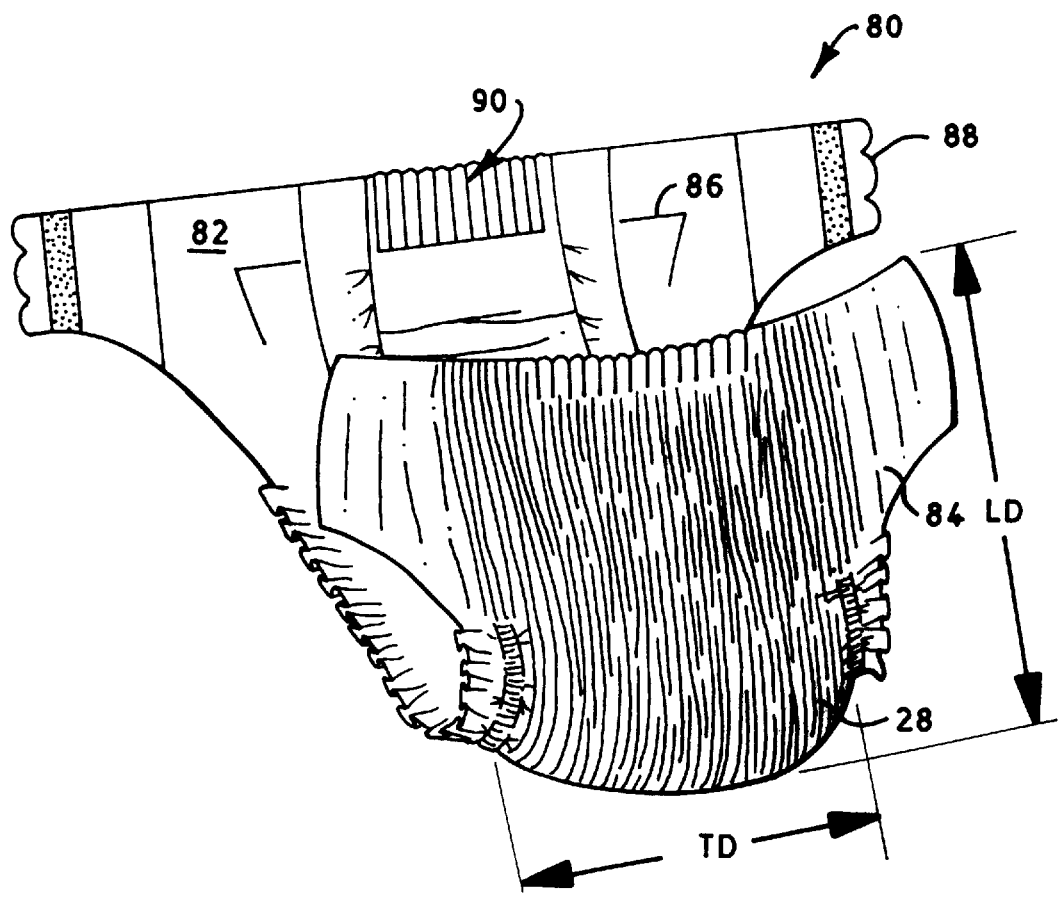
FIG. 4 is a partially cut-away top plan view of an exemplary personal care absorbent article, in this case a diaper, which may utilize the necked laminate to form the liquid transfer material according to the present invention.

As has been stated previously, the necked laminate 2 may be used in a wide variety of applications, including personal care absorbent articles or garments such as diapers, training pants, incontinence devices and feminine hygiene products such as sanitary napkins. An exemplary article 80, a diaper, is shown in FIG. 4. Referring to FIG. 4, most such personal care absorbent articles 80 include a liquid permeable top sheet or liner 82, a back sheet or outercover 84 and an absorbent core 86 disposed between and contained by the liner 82 and back sheet 84. Articles 80, such as diapers, may also include some type of fastening means 88 such as adhesive fastening tapes or mechanical hook and loop type fasteners to maintain the garment in place on the user.

Figure 16:
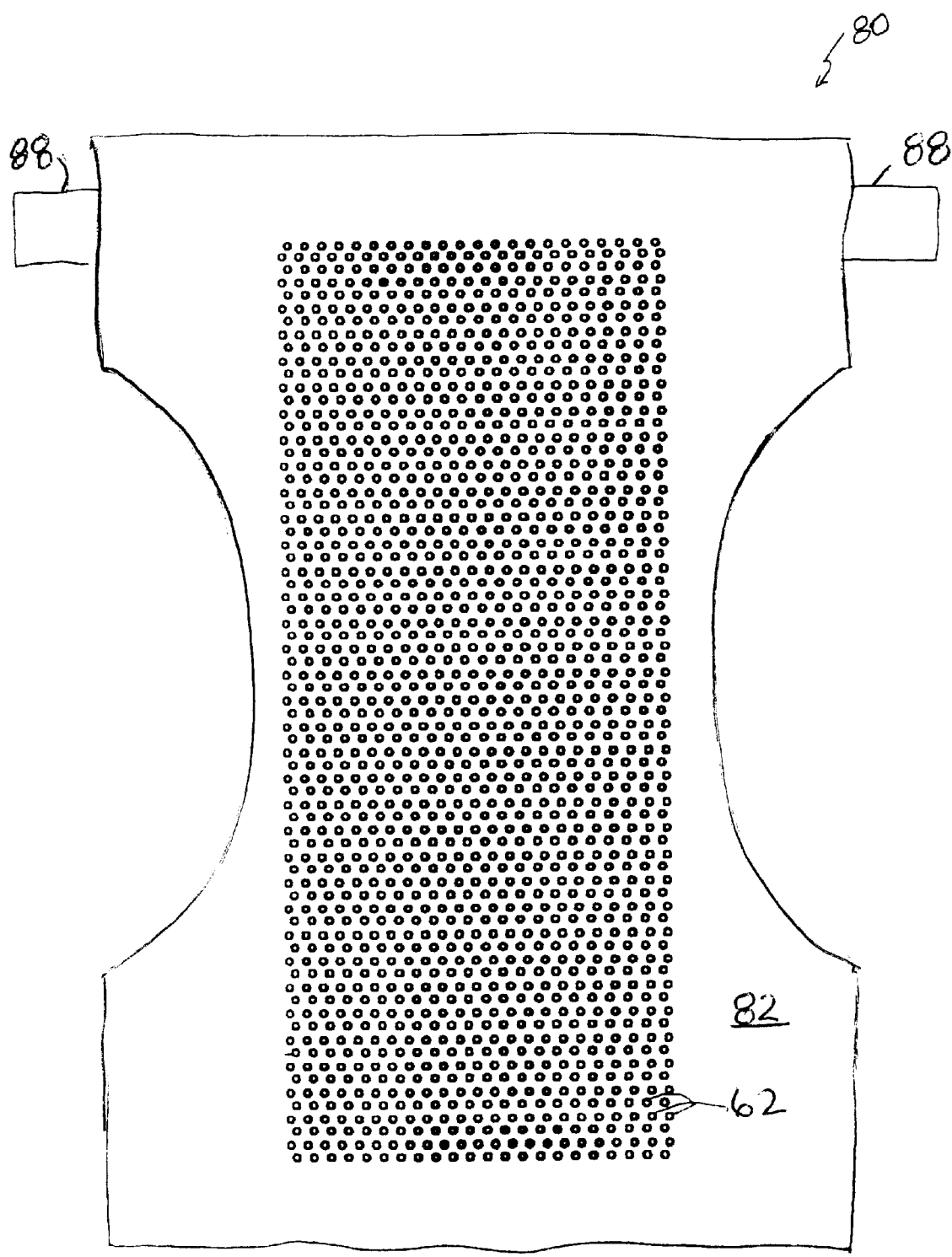
FIG. 16 is a top plan view of an exemplary article with an exemplary aperturing pattern for use in the liquid transfer material of the present invention.

The necked laminate 2 may be used to form various portions of the article including, but not limited to the liner 82. If the necked laminate is to be used as the liner 82, it will be apertured or otherwise made to be liquid permeable. Such apertures are preferably conical in shape, but may be shaped otherwise to improve the flow of liquid therethrough. Turning to FIG. 16, a top plan view of a diaper 80 with an exemplary aperturing pattern is shown. The liquid transfer material, in this case liner 82, with apertures 62, is made from the necked laminate as described herein. The liner 82 exhibits good liquid transfer, while allowing flexibility to the diaper in the form of extensibility and retractability due to the nature of the laminate. As the necked laminate has TD extensibility and retractability, the liner 82 will also stretch, recover, and generally fit the baby much better in that the liner will have the same extensibility as other portions of the diaper.

Figure 18:
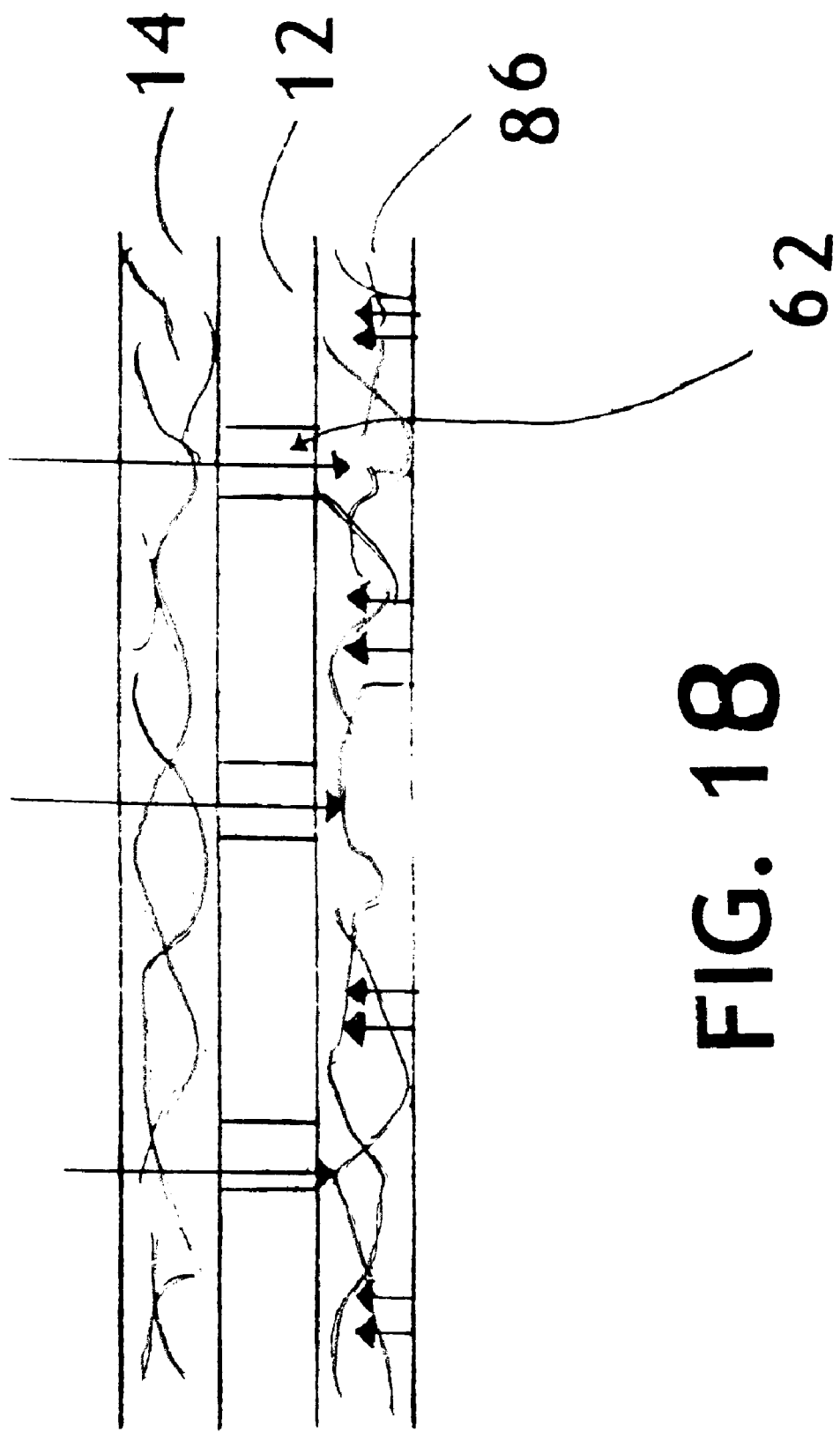
FIG. 18 is a cross-section of the apertured liquid transfer material, wherein the arrows indicate liquid flow through the material.

FIG. 18 shows a cross-section of an apertured liquid transfer material attached to absorbent core 86, wherein the arrows indicate liquid flow through the material. In other words, the liquid transfer material of the present invention including the laminate 2, when used for instance as a liner 82 of a diaper 80, would allow the liquid to flow through the apertures 62 in the liner 82., but would essentially keep the liquid from leaking back out of the liner 82. As shown by the arrows, the liquid will generally move in one direction through the apertures or slits 62 and will most likely be absorbed by the underlying absorbent core 86 before it is allowed to flow in the opposite direction, i.e. back out of the apertures 62. In the unlikely event that the liquid is not immediately captured by the underlying absorbent core 86, the only route for leaking back out of the liquid transfer material would be to find the aperture or slit 62 again. The more likely event will be that the liquid will be stopped by the non-apertured portion of the liner 82.

Necked laminates forming the liquid transfer material of the present invention are also useful in articles used in medical applications. Referring to FIG. 5, the necked laminate 2 has been utilized to form an exemplary article, in this case a facemask 60. The necked laminat 2 is gathered by fastening means 88' to tie the facemask 60 to the head of a wearer. In this application, the non-elastic film layer would most likely be apertured so that the wearer may breathe comfortably. Such apertures 62 will be sized and located such that breathing is not impaired but will not be too large or numerous such that the function of the facemask (e.g. to protect the user) is thwarted. One such embodiment may be to have the apertures on the TD edges of the facemask.

Yet another exemplary article is a garment such as a lab coat or workwear. One particularly bothersome aspect of use of the prior art non-elastic laminate is the lack of "give" as discussed above. This can be best understood in the context of bending a laminate-clad elbow. If the prior art laminate was used to create the garment, when the elbow bends, the material tightens around the elbow which may cause the material to tear or at the very least cause discomfort to the wearer. If the garment were to be made of a liquid transfer material of the present invention including the necked laminate, however, the material will "give" when the elbow bends and afterwards tend to return to its prior form. The laminate would not recover with a strong force but very gently so comfort would be maintained. The apertures would be properly sized and located to increase overall breathability but not affect the desired protection.

One advantage of using necked laminat 2 in such applications is that the articles will be more "cloth-like" in both appearance and feel. Additionally, the transverse extensibility and retractability will allow the article to more closely conform to the body of the user.

The liquid transfer material of the present invention including the necked laminate is able to maintain properties such as strength, hydrohead (barrier) and breathability in the non-apertured areas while getting improvements in "cloth-like" characteristics such as conformability and transverse extensibility and retractability. The advantages and other characteristics of the present invention are best illustrated by the following examples.

EXAMPLES

Samples of the present invention were prepared as described below. The samples were then subjected to the following tests:

Tensile Test: The tensile test measured strength and elongation or strain of a fabric when subjected to unidirectional stress according to ASTM Standard Test D 5034-95, as well as Federal Test Methods Standard No. 191A Method 5102-78. This test measured the strength in pounds and percent stretch while elongating the sample until it broke. Higher numbers indicate a stronger and/or more stretchable fabric, respectively. The term "peak load" means the maximum load or force, expressed in pounds, required to elongate a sample to break or rupture in a tensile test. The term "strain" or "percent stretch" means the increase in length of a sample during a tensile test expressed as a percentage. Values for peak load and strain at peak load were obtained using a width of fabric of 3×6 in. (76×152 mm), a 3 in. (76 mm) clamp width, a gauge length of 3 in. (76 mm), and a constant rate of extension of 12 inches/min. (305 mm/min.), where the entire sample width was gripped in the clamps.

The specimen was clamped, for example, in an 1130 Instron, available from the Instron Corporation, or a Thwing-Albert Model INTELLECT II available from the Thwing-Albert Instrument Co., 10960 Dutton Rd., Philadelphia, Pa. 19154, and the unit was zeroed, balanced and calibrated according to the standard procedure.

Breathability Test: The water vapor transmission rate (WVTR) for the sample materials was calculated generally in accordance with the following test method in order to measure the breathability of the samples. The test procedure establishes a means to determine the normalized rate of water vapor transmission through solid and porous films, nonwoven materials, and other materials while under steady state conditions. The material to be evaluated is sealed to the top of a cup of water and placed in a temperature-controlled environment. Evaporation of water in the cup results in a relatively higher vapor pressure inside the cup than the vapor pressure of the environment outside of the cup. This difference in vapor pressure causes the vapor inside the cup to flow through the test material to the outside of the cup. The rate of this flow is dependent upon the permeability of the test material sealed to the top of the cup. The difference between the beginning and ending cup weights is used to calculate the water vapor transmission rate.

In particular, circular samples measuring three inches in diameter were cut from each of the test materials and a control which was a piece of CELGARD® 2500 film from Hoechst Celanese Corporation. CELGARD® 2500 film is a microporous polypropylene film. The test dish was a 68-1 Vapometer cup distributed by Thwing-Albert Instrument Company of Philadelphia, Pa. One hundred milliliters of water were poured into each Vapometer cup and individual samples of the test materials and control material were placed across the open tops of the individual cups. A rubber gasket and metal ring (fitted to the cup) were placed over the sample and clamped using metal clamps. The sample test material and control material were exposed to room temperature over a 6.5 centimeter diameter circle, having an exposed area of approximately 33.17 square centimeters. The cups were placed in an oven at about 38 ° C. (100° F.), long enough for the cups to reach thermal equilibrium. The cups were removed from the oven, weighed, and replaced in the oven. The oven was a constant temperature oven with external air circulating through it to prevent water vapor accumulation inside. A suitable forced air oven is, for example, a Blue M Power-O-Matic 60 oven distributed by Blue M. Electric Company of Blue Ispeak, Ill. After 24 hours, the cups were removed from the oven and weighed again. The preliminary test water vapor transmission rate values were calculated with Equation (I) below:

$$\text{APP MVT} = (\text{grams weight loss over 24 hours}) \times 7571/24 \text{ expressed in } g/m^2/24 \text{ hours} \qquad (I)$$

Approximate moisture vapor transfer is designated by "APP MVT". Under the predetermined set conditions of about 38° C. (100° F.) and ambient relative humidity, the WVTR for the CELGARD® 2500 control has been defined to be 5000 grams per square meter for 24 hours. Accordingly, the control sample was run with each test and the preliminary test values were corrected to set conditions using Equation (II) below:

$$\text{WVTR} = (\text{Test WVTR/control WVTR}) \times (5000 \ g/m^2/24 \ \text{hours}) \qquad (II)$$

Hydrohead: A measure of the liquid barrier properties of a fabric is the hydrohead test. The hydrohead test determines the height of water (in centimeters) which the fabric will support before a predetermined amount of liquid passes through, usually 3 drops. A fabric with a higher hydrohead reading has a greater barrier to liquid penetration than a fabric with a lower hydrohead. The hydrohead test is performed according to Federal Test Standard 191A, Method 5514 using a Textest FX-3000 Hydrostatic Head Tester available from Marlo Industries, Inc., P.O. Box 1071, Concord, N.C. A circular head having an inner circumference of 26 cm was used to clamp down the sample.

% Theoretical Extensibility: The % Theoretical Extensibility is the amount of extensibility that can be expected for necked laminates of the present invention, based upon how much the original width is reduced and assuming the original laminate has no inherent extensibility. In the following equations, original width is the un-necked width (transverse dimension) of the laminate, while necked width is the width of the laminate after necking. % Theoretical Extensibility can be determined as follows:

% Theoretical Extensibility=100×[(original width÷necked width)÷necked width]

which can be rewritten as:

% Theoretical Extensibility=100×[(original width÷necked width)−1]

The % of the original width that the laminate is necked can be represented by the following equation:

% original width=100×(necked width÷original width)

which can be rewritten as:

(original width÷necked width)=100÷% original width

Substituting this equation into % Theoretical Extensibility above:

% Theoretical Extensibility=100×[(100÷% original width)−1]

So, for each sample below, the original width was measured, as was the necked width, and % Theoretical Extensibility was calculated as shown below in Table 3.

% Permanent Set: The permanent set test measures the degree of retractability of a material after being stretched to a specific length. Generally, the greater the permanent set value, the less retractable the sample is. After the laminate was produced and wound onto a roll, indelible ink was used to mark a 2 in. (5.08 cm) wide strip of material in the transverse dimension. After the laminate was unwound, a sample area 3 in. (7.62 cm) (LD)×4.5 in. (11.43 cm) (TD) was cut out of the laminate to include the marked-off area. Each sample was placed between two 3 in. (7.62 cm) wide jaws. The jaws were separated a distance of 2 in. (5.08 cm) apart and the jaws were clamped on the marks that were previously made on the material. The samples were then elongated a specified amount; 90% or 1.8 in. (4.57 cm), and allowed to retract. The elongation was recorded when the force during retraction reached 25 grams. The permanent set was calculated as follows:

% Permanent set=100×(distance×between the jaws when the resistance of the laminate equaled 25 grams$_{force}$ during the retraction cycle−initial length)÷total stretched length=[×(in.)−2 (in.)] ÷1.8 =[×(cm)−5.08 (cm)]÷4.57

Three repetitions were performed and the average valve is represented in the Example below.

Cycle Test: The samples were also cycled on the Instron tester with Microcon II using a 50 kg load cell. The sample sizes and tester were set up as described above except that the gage length was 2 inches (5.08 cm). Chart and crosshead speeds were set for 20 inches (50.8 cm) per minute. The maximum extension limit for the cycle length was set at a distance determined by calculating 50 percent of the "elongation to break" from the Tensile Test. The samples were cycled to the specified cycle length two times and then were taken to break on the third cycle. The test equipment was set to measure Peak Load in grams force for each cycle. On the third cycle (cycle to break), the Peak Elongation and Peak Load were measured.

Liner Runoff: The liner runoff test was used to measure the ability of a material to allow the penetration of fluid. The procedure used was similar to that described in U.S. Pat. No. 5,258,221 to Meirowitz et al., which is incorporated by reference herein in its entirety. In the procedure used herein, 50 ml of 0.85% saline solution (at room temperature) was dispensed onto an 8 in.×5.25 in. (20.3 cm×13.3 cm) sample of liner that was placed on a coform absorbent having a basis weight of 190 gsm as described in more detail below in Example 3. The materials were placed on a flat surface that was sloped at a 45 degree incline. The coform absorbent was utilized as a retention material and was placed beneath the liner to absorb the fluid that penetrated the liner. The fluid that was not transmitted to the retention material would run off, be collected, and weighed. Three repetitions were performed with new absorbent and liquid.

Diaper Runoff: The diaper runoff test was used to measure the ability of a material to allow the penetration of fluid. The procedure used was similar to that described in U.S. Pat. No. 5,258,221 to Meirowitz et al., which is incorporated by reference herein in its entirety. In the procedure used herein, 100ml of 0.85% saline solution (at room temperature) was dispensed onto a 15 in.×5.25 in. (38.1 cm×13.3 cm) sample of liner that was placed on a coform absorbent having a basis weight of 190 gsm to simulate a diaper as described in more detail below in Example 3. The materials were placed on a flat surface that was sloped at a 30 degree incline. The coform absorbent was utilized as a retention material and was placed beneath the liner to absorb the fluid that penetrated the liner. The fluid not transmitted to the retention material and absorbed will run off, be collected, and weighed. Three repetitions were generally performed, and both the liner sample and the retention fluid were replaced between repetitions.

Fluid Intake Flowback Evaluation (FIFE): Tests were conducted using a FIFE tester (not shown). The FIFE tester had two PLEXIGLASS plates. The top plate of the FIFE tester included a cylinder having an inner diameter of 2 inches (5.08 cm). The top plate had a circular hole formed in the center thereof. The cylinder extended upwardly substantially perpendicular to the surface of the top plate. The cylinder fit within the circular hole and was secured therein by an adhesive. The adhesive permanently secured the cylinder as an integral part of the top plate and prevented liquid from leaking outwardly onto the top surface of the top plate. Pin elements were located near outside corners of the bottom plate. The pin elements were aligned with apertures in the top plate to mount the plates together. A funnel was placed at the top of the cylinder to pour liquid into the test device. The combined mass of the top plate of the FIFE tester including the cylinder, and the funnel was from 900 to 1100 grams.

The test samples were prepared as described below for Example 4. The samples were placed in the FIFE tester such that the article was placed between the top and bottom plates. In use, the bottom plate and top plate of the FIFE tester define substantially horizontal planes. The sample was centered such that the cylinder of the top plate was above the center of the sample. The test began with a first insult of 80 milliliters of saline solution being poured rapidly into the test cylinder via a funnel placed atop the cylinder. After a one minute wait, a second 80 milliliter insult was poured into the FIFE cylinder. A third and final insult of 80 milliliters was applied after another one minute delay. A final one minute delay was added.

Flowback Test: The test specimen from the FIFE test above was tested for flowback after the second 80 ml insult. The specimen is placed on a vacuum box with two 3.5×12" tared pieces of blotter paper (1 on top of the other) placed on top of the specimen on the target zone. A pressure of 0.5 psi was applied for a period of 2 minutes. After the 2 minute interval, the blotter paper was removed and weighed and the amount of fluid absorbed by the blotter paper was measured in grams. Higher values were an indication of a greater degree of flowback for the particular material tested. Additional discussion of these tests may be found in U.S. Pat. No. 5,536,555, commonly assigned.

Example 1

A non-apertured necked laminate was prepared from a non-elastic film layer and a non-elastic nonwoven web layer. A 1.5 mil layer of blown film made of 48% by weight (25 volume percent) SUPERCOAT calcium carbonate as manufactured by English China Clay America, Inc. of Sylacauga, Ala., 47% by weight (68 volume percent) linear low density polyethylene (LLDPE) available under the trade designation DOWLEX NG3347A as manufactured by the Dow Chemical Company ("Dow"), 5% by weight (7 volume percent) low density polyethylene (LDPE) available under the trade designation 6401 as manufactured by Dow, and 2000 ppm antioxidant stabilizer available under the trade designation B900 as manufactured by Ciba Specialties Company of Tarrytown, N.Y. The film layer, made of the composition as described above was pre-made and wound onto a roll. To make this film layer highly breathable, it should be stretched over about 4×(4 times its original length). The film layer was then unwound from a film unwind unit into a conventional machine direction orienter, such as that manufactured by the Marshall and Williams Company, where it was partially stretched as shown in Table 1 below (stretching draw) in the machine direction to form a partially stretched, breathable film layer. Likewise, a 0.4 osy basis weight standard polypropylene spunbond having a wireweave bond pattern such as that made by the Kimberly-Clark Corporation of Dallas, Tex., was unwound and an adhesive of 3 gsm weight (at the application point) available as H2525A from Ato-Findley of Wauwatosa, Wis. was applied to one surface of the nonwoven web layer using an air assisted spraying device such as a meltblown device as described in Butin et al., supra. Such devices are generally described in, for example, commonly assigned U.S. Pat. No. 4,949,668 to Heindel et al.; U.S. Pat. No. 4,983,109 to Miller et al., assigned to Nordson Corporation; and U.S. Pat. No. 5,728,219 to Allen et al., assigned to J&M Laboratories, Inc.

The adhesive side of the nonwoven web layer was then laminated to the partially stretched film layer using laminating rollers at a pressure of 30 pli (5.4 kg/linear cm) of a smooth resilient (rubber coated) anvil roll on one side and a smooth, unheated, steel roll.

Figure 10:
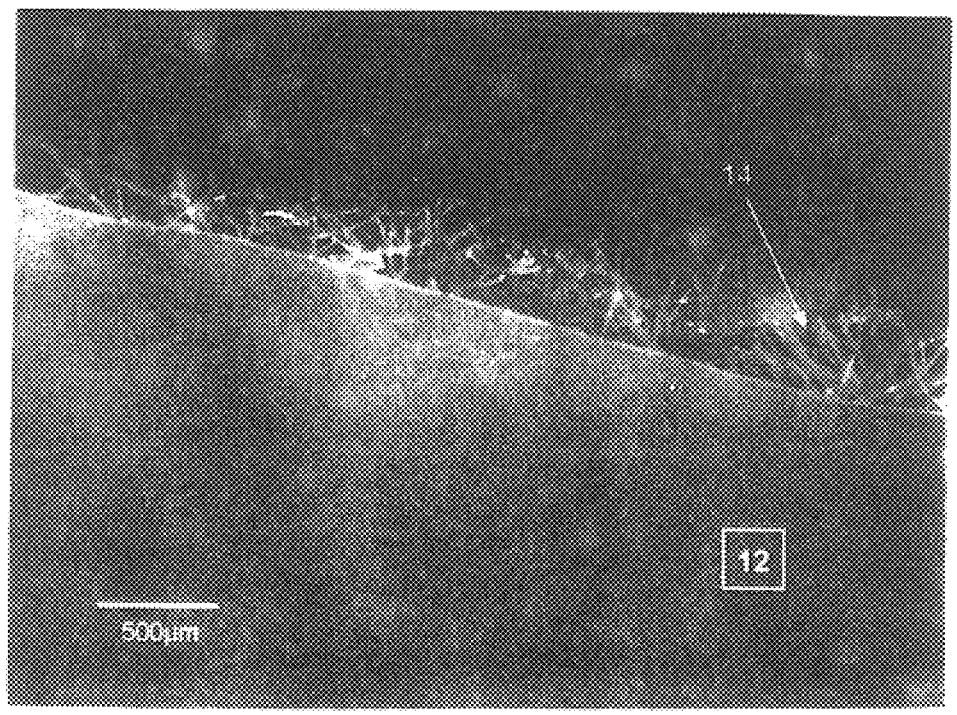
FIG. 10 is an oblique view of an optical photomicrograph of a prior art laminate.

The laminate was then stretched in the longitudinal dimension and necked in the transverse dimension by passing it through a stretch nip that was operating at a greater speed than the speed than the laminating rollers (see Table 1 below —the Laminate Necking Draw column). The necking draw caused contraction (necking) of the laminate in the transverse direction. The laminating rollers were spaced about 8 feet (2.4 m) from the stretch nip. "Total draw" in Table 1 is the necking draw multiplied by the stretching draw and was sufficient to insure enough orientation or stretching of the film layer to make it highly breathable. The thus formed transversely extensible and retractable necked laminate was then wound onto a roll. Samples were cut from the necked laminate and subjected to tests, the results of which are reported below in Table 1. Samples C1 and C2 are comparative (baseline) examples wherein the film layer was stretched as indicated, but the laminate was not necked. FIG. 10 shows an oblique image of a prior art laminate of Sample C1, wherein the film layer 12 was fully stretched prior to lamination to the neckable material 14 to form the laminate that was not subsequently necked. Sample 8 was a repeat of Sample 7. "Peak strain" is the strain at "peak load".

TABLE 1

| Sample | Total Film Draw | Film Stretching Draw | Laminate Necking Draw | WVTR g/m²/24 hr | Hydrohead mbar | LD Peak Strain % | LD Peak Load lb. (kg) | TD Peak Strain % | TD Peak Load lb. (kg) |
|---|---|---|---|---|---|---|---|---|---|
| C1 | 5.0X | 5.0X | 1.0X | 2799 | 353 | 35.7 | 25.62 (11.62) | 92.2 | 5.11 (2.32) |
| C2 | 3.6X | 3.6X | 1.0X | 1759 | 265 | 66.4 | 23.36 (10.59) | 100.8 | 6.16 (2.79) |
| 3 | 3.9X | 3.6X | 1.1X | 1004 | 316 | 65.6 | 26.33 (11.94) | 100.0 | 6.15 (2.79) |
| 4 | 4.3X | 3.6X | 1.2X | 886 | 437 | 69.1 | 30.75 (13.95) | 95.0 | 6.01 (2.73) |
| 5 | 4.6X | 3.6X | 1.3X | 1474 | 383 | 65.2 | 33.32 (15.11) | 126.9 | 5.43 (2.46) |
| 6 | 5.0X | 3.6X | 1.4X | 1213 | 454 | 55.6 | 44.07 (19.99) | 197.8 | 4.99 (2.26) |
| 7 | 5.2X | 3.6X | 1.45X | — | 383 | 48.8 | 35.01 (15.88) | 144.3 | 5.46 (2.48) |
| 8 | 5.2X | 3.6X | 1.45X | 1140 | 387 | 56.0 | 40.20 (18.23) | 141.2 | 4.70 (2.13) |

Figure 11A:
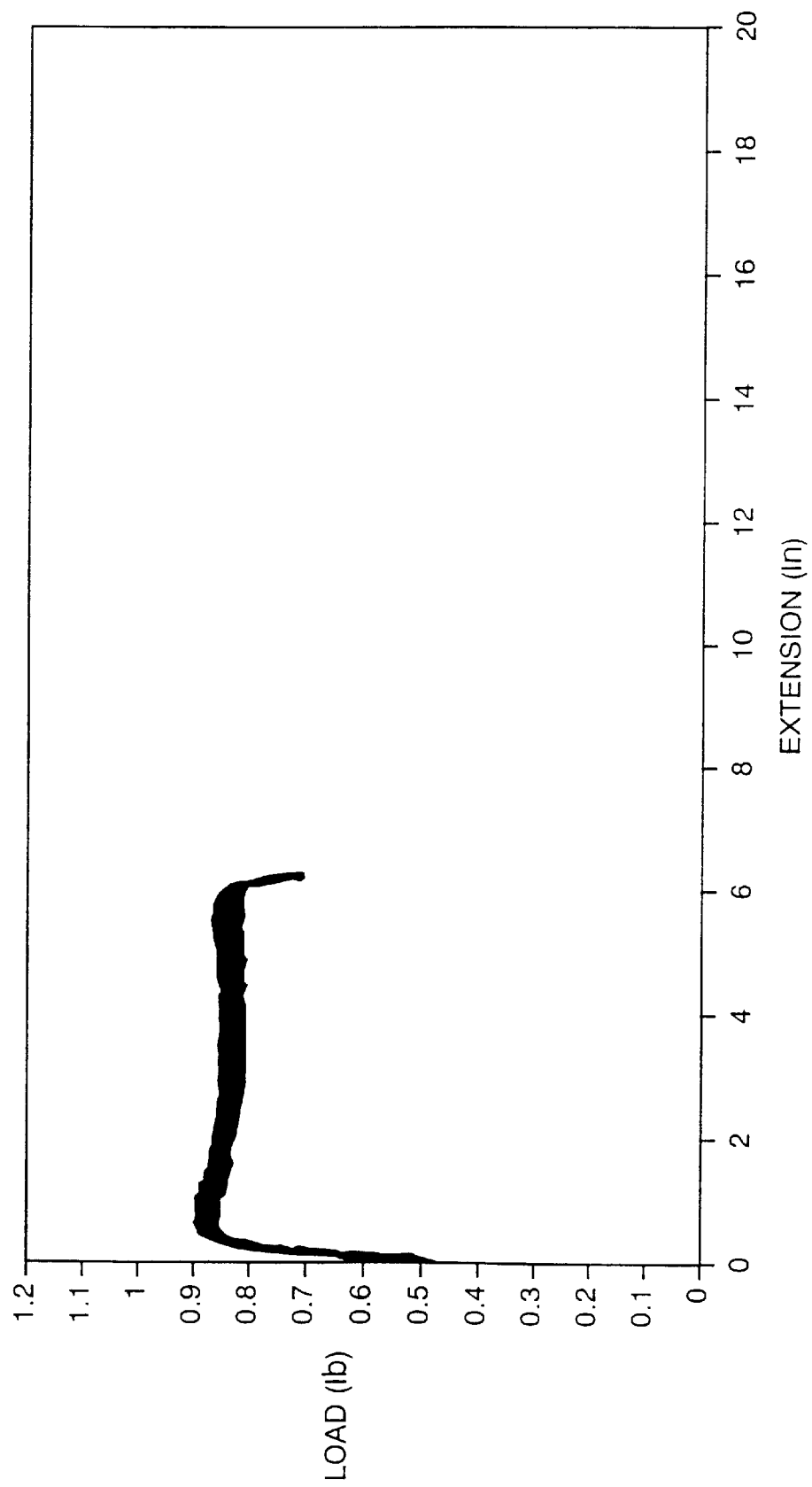
FIGS. 11a, b, and c, and 12a, b, and c, graphically illustrate load versus extension curves for various samples.
Figure 11B:
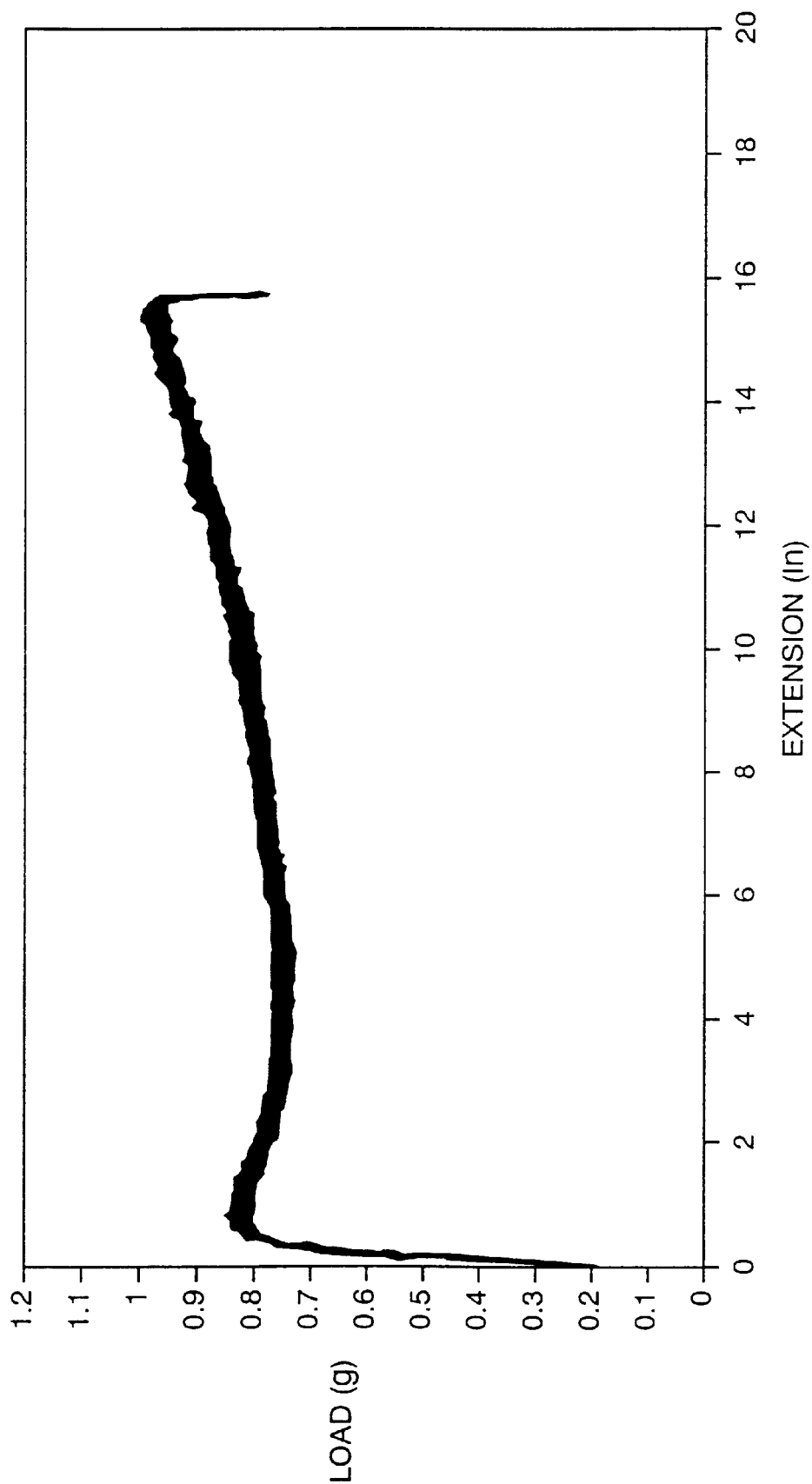
Figure 11C:
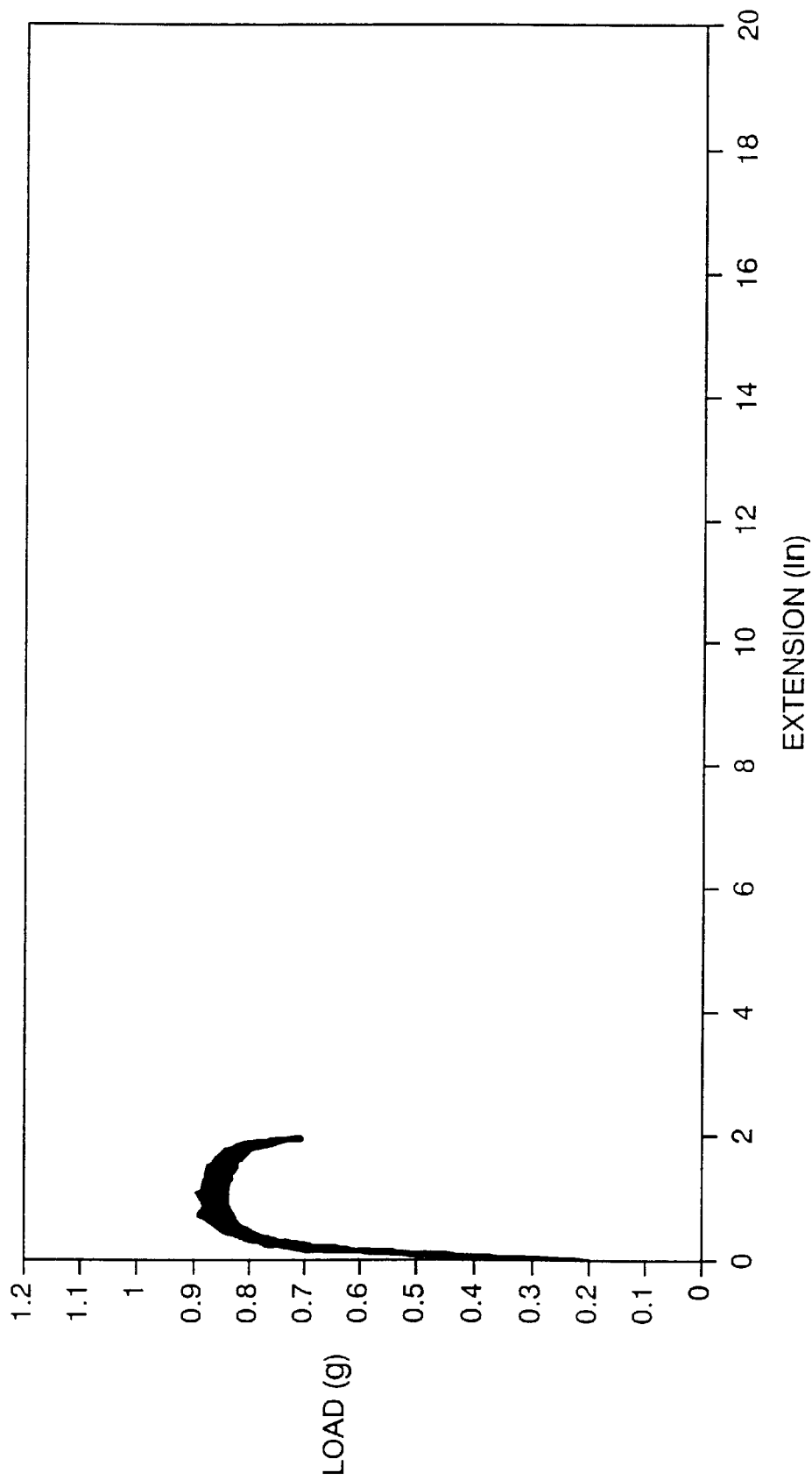
Figure 12A:
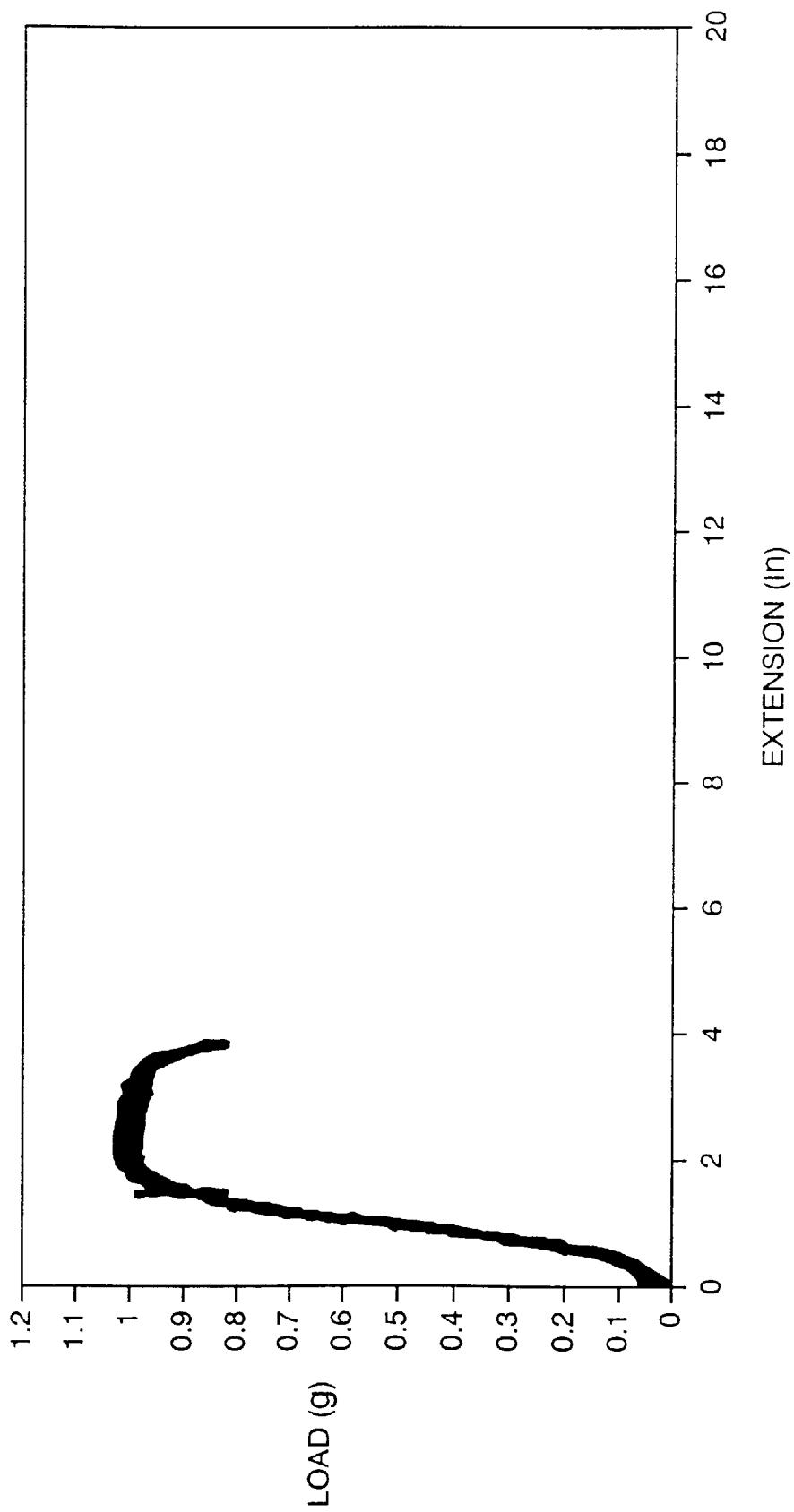
Figure 12B:
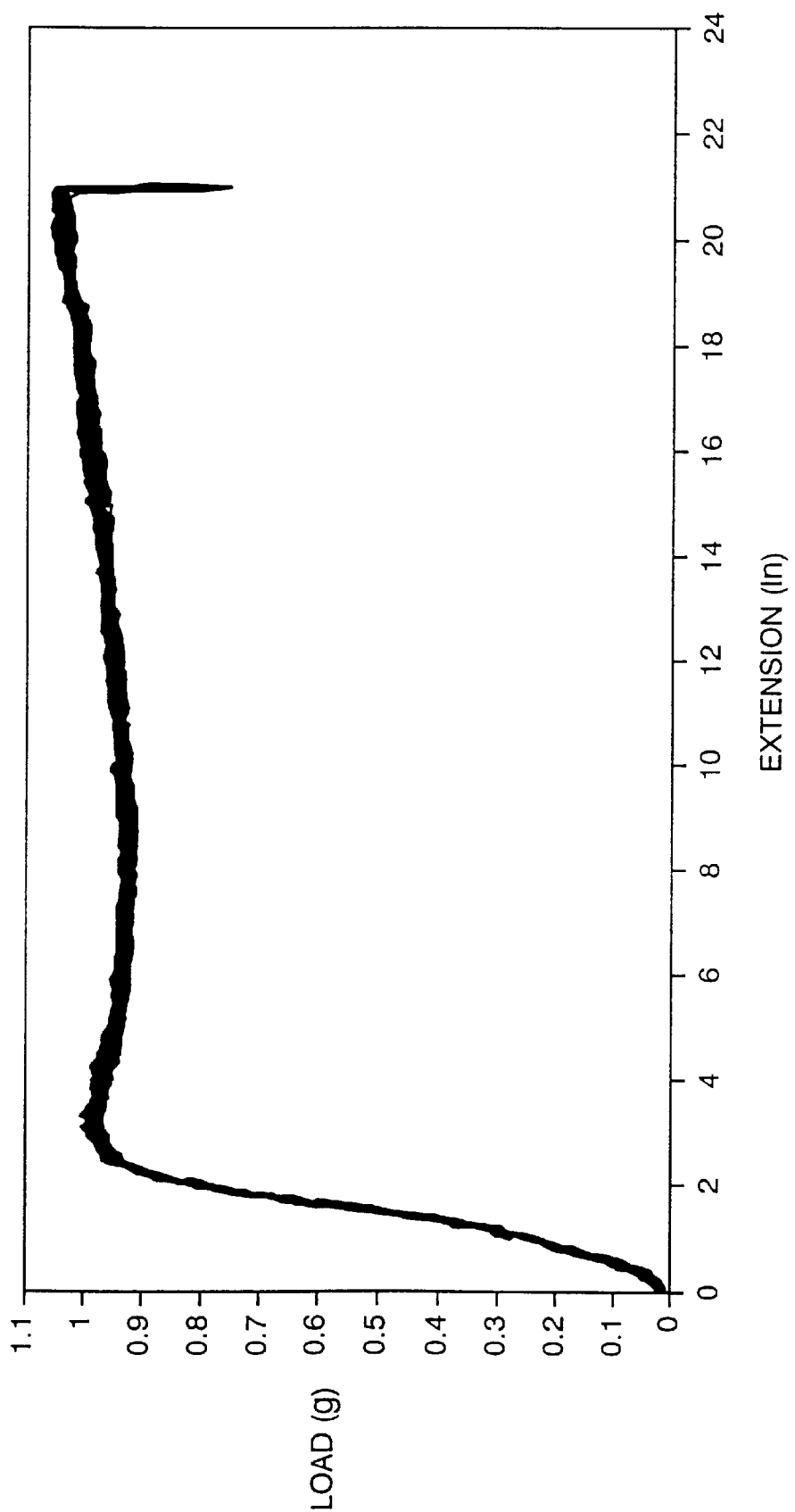
Figure 12C:
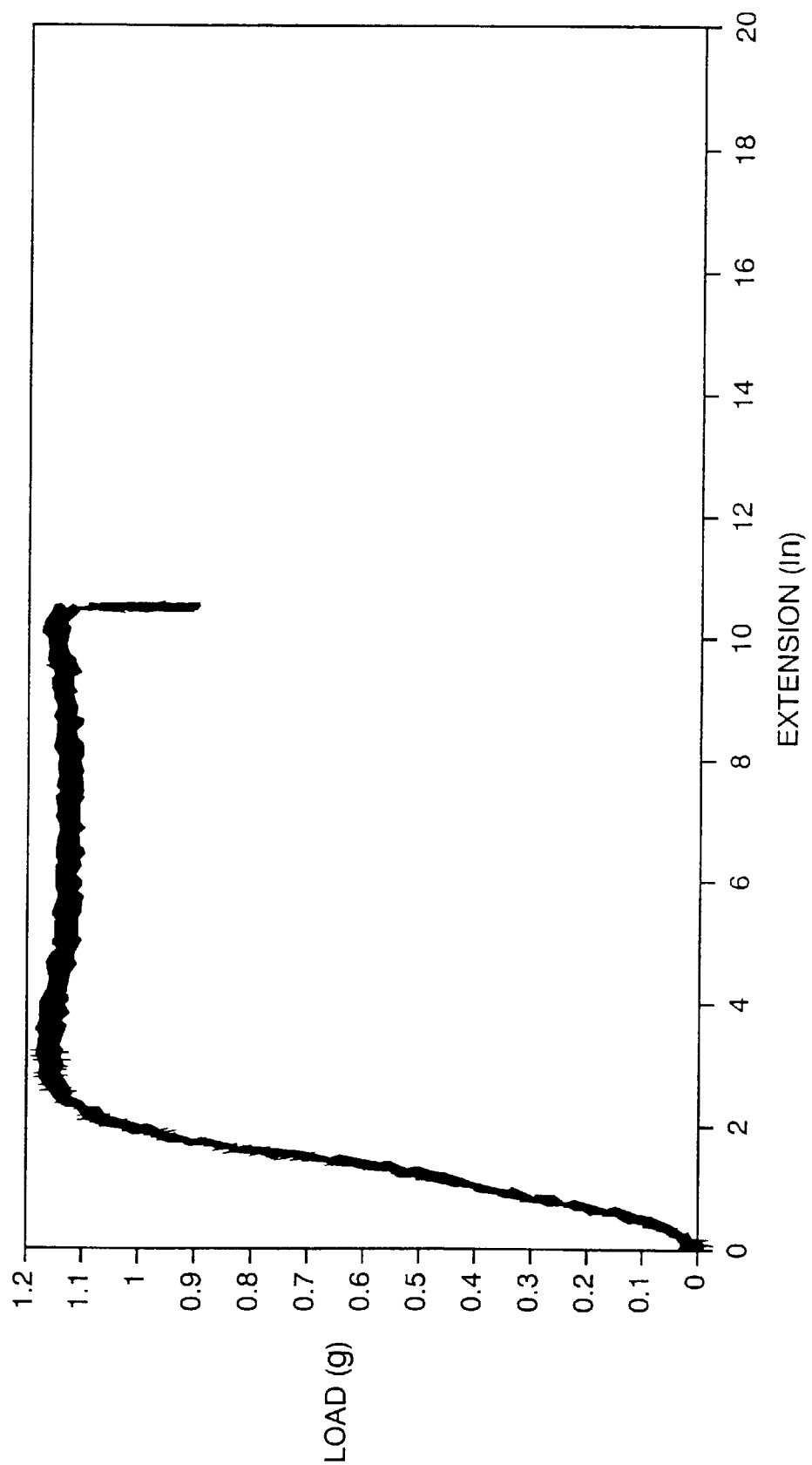
Figure 14:
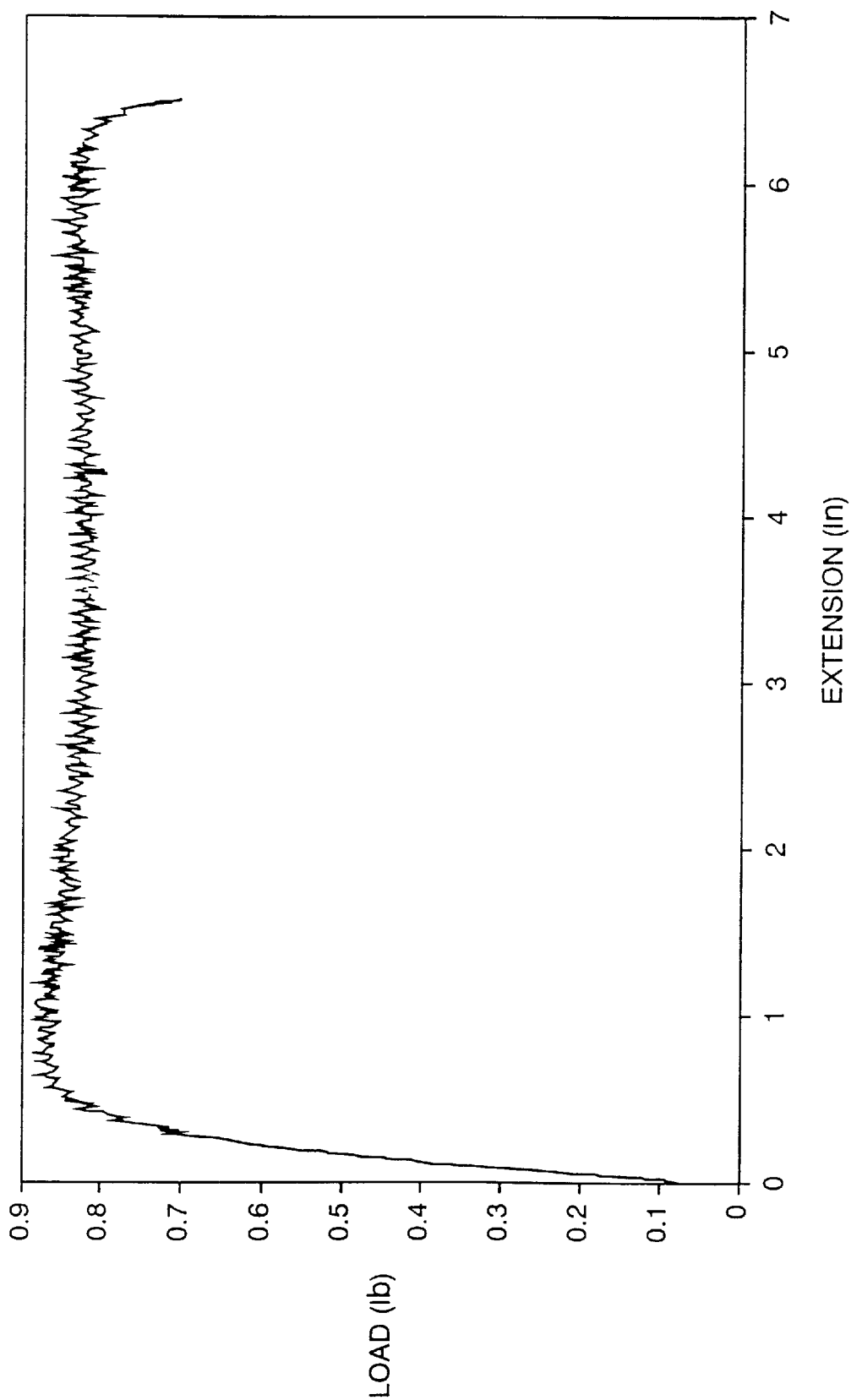
FIGS. 14–15 graphically illustrate enlarged curves of load versus extension for various samples.
Figure 15:
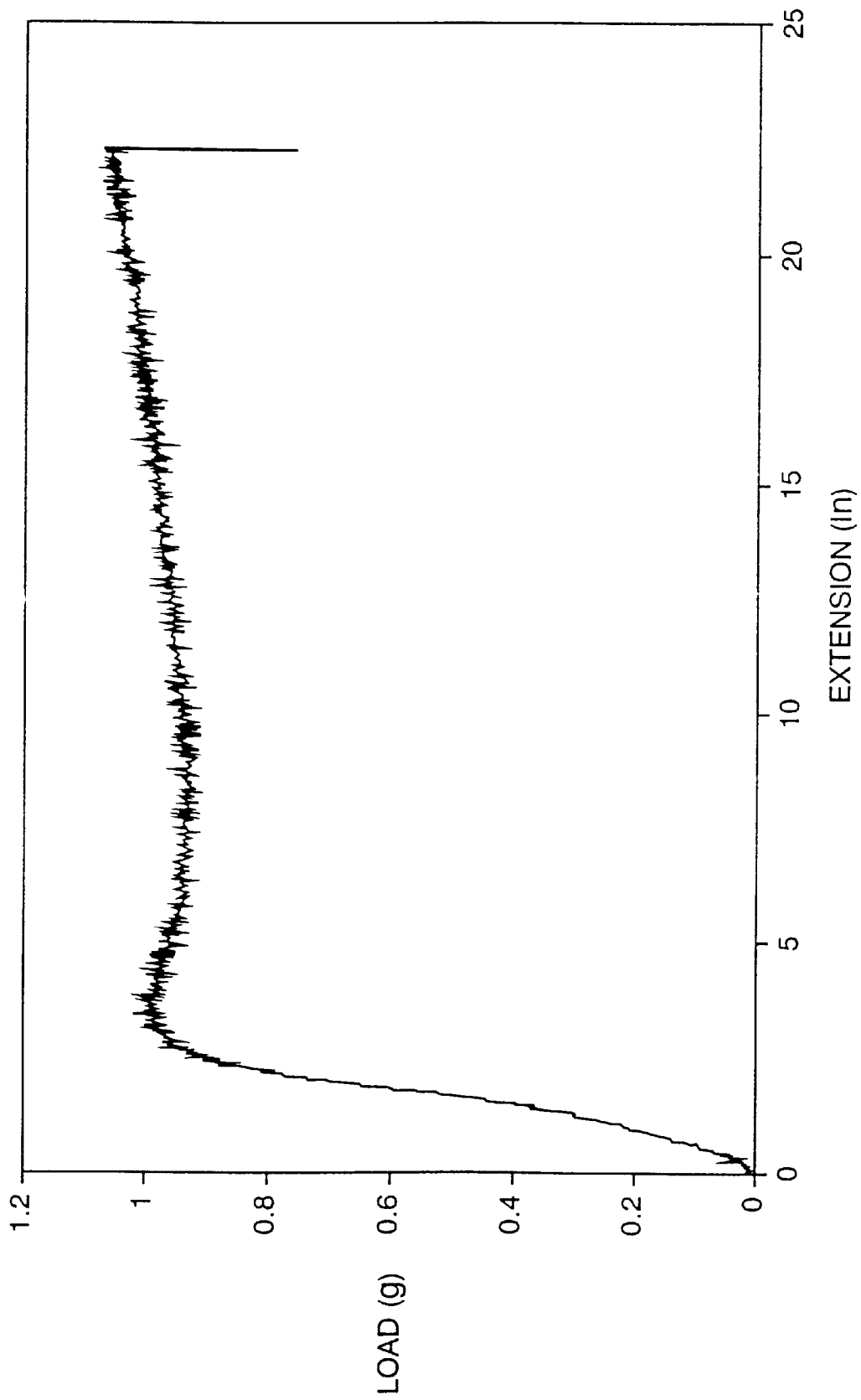

Sample 6 had the highest TD peak strain. In this laminate, the film layer has been drawn a total of 5.0X, which is typical drawing for such articles. The laminate has additionally been necked by a 1.4×draw. The film layer of Sample C1 has also been drawn a total of 5.0X, but the laminate has not been necked at all. Even though the film layers have been drawn by the same amount, the example of the present invention, Sample 6, has a much greater TD peak strain than the comparative example, which is an indication of the improvement of the transverse extensibility of the present invention. FIGS. 11a, b, and c, and 12a, b, and c, graphically illustrate load versus extension curves for Samples C1 and 6, while FIGS. 14–15 graphically illustrate enlarged curves of load versus extension curves for these samples. FIGS. 11a, b, and c relate to three replicates of the delaminated film layer of Sample C1, whereas FIGS. 12a, b, and c relate to three replicates of the delaminated film layer of Sample 6, having the striated rugosities.

Table 3 below represents necked width in inches (cm) as a function of percent stretch and shows how readily the necked laminates elongated in the transverse direction for each of the samples of Table 1. From the tensile strength test above, the force in pounds (kilograms) was recorded below in Table 2 for each sample at 30%, 60%, 90%, 120%, 150%, and 180%. The laminates which had been necked to a narrower width (Samples 5, 6, 8; Table #3 "Laminated Necked Width" column) elongated at a much less force at the same % elongation than the control and to a much greater extent before breaking. If the sample broke either on or before the percent step change, it has been designate as "- - -".

TABLE 2

| Sample | 30% | 60% | 90% | 120% | 150% | 180% |
|---|---|---|---|---|---|---|
| C1 | 2.51 | 4.21 | 5.05 | — | | |
| | (1.14) | (1.91) | (2.29) | | | |
| C2 | 3.16 | 5.05 | 6.02 | — | | |
| | (1.43) | (2.29) | (2.73) | | | |
| 3 | 2.74 | 4.88 | 5.88 | — | | |
| | (1.24) | (2.21) | (2.67) | | | |
| 4 | 2.78 | 4.89 | 5.92 | — | | |
| | (1.26) | (2.22) | (2.69) | | | |
| 5 | 1.30 | 2.84 | 4.41 | 5.27 | — | |
| | (0.59) | (1.29) | (2.00) | (2.39) | | |
| 6 | 0.60 | 1.28 | 2.13 | 3.22 | 4.09 | 4.73 |
| | (0.27) | (0.58) | (0.97) | (1.46) | (1.86) | (2.15) |
| 7 | 1.51 | 2.78 | 4.18 | 5.06 | 5.38 | — |
| | (0.68) | (1.26) | (1.90) | (2.30) | (2.44) | |
| 8 | 1.21 | 2.33 | 3.42 | 3.89 | 4.47 | — |
| | (0.55) | (1.06) | (1.55) | (1.76) | (2.03) | |

Table 3 shows the calculated % Theoretical Extensibility as described above for each of the samples of Table 1.

TABLE 3

| Sample | Laminate Necked Width in. (cm) | % Original Width | % Theoretical Extensibility |
|---|---|---|---|
| C1 | 12⅜ (31.43) | 100 | 0 |
| C2 | 12¼ (31.12) | 99 | 1 |
| 3 | 11½ (29.21) | 93 | 7.5 |
| 4 | 10¾ (27.31) | 87 | 15 |
| 5 | 8¾ (22.23) | 71 | 41 |
| 6 | 7½ (19.05) | 61 | 65 |
| 8 | 6⅜ (16.19) | 51 | 94 |

The breathability was measured by WVTR for the necked laminate when it was in extended configuration, since this is the configuration it would have when in use as for instance in a diaper. Three repetitions of Sample 6 were extended 100% and 166% and tested for WVTR. The results were as follows in Table 4.

TABLE 4

| Sample 6 | WVTR $g/m^2/24$ hr |
|---|---|
| Unstretched (from Table 1 above) | 1213 |
| 100% extended | 3960 |
| 166% extended | 4250 |

To better describe the TD extensibility of the film layer, for Samples C1 and 6 above, the film layer was delaminated from the spunbond layer for a further test. Prior to delamination, a length of 3 inches (7.62 cm) was marked on the film side of the laminate across the TD. The delamination was conducted by completely immersing and soaking the laminate in denatured ethyl alcohol (ethanol) which softened and partially dissolved the adhesive bonding between the film layer and spunbond layer, such that the striated rugosities of the film layer were not removed, damaged, or otherwise distorted. Once delaminated, the film layer was tested in a tensile tester as described above and the force was measured when the film layer had been extended by 0.3 inches (0.762 cm) (10% strain). The force required to extend Sample C1 (the average of three repetitions) was approximately 1000 grams per mil of the film layer thickness. The force required to extend Sample 6 (the average of three repetitions), on the other hand, was approximately 60 grams per mil of the film layer thickness, which was the thickness determined with the striated rugosities flattened out.

Example 2

Additional non-apertured laminates were prepared as described above, except that a non-elastic adhesive was used in some samples and that some samples were heated after being necked. The modifications were made to evaluate the impact of: 1) using a non-elastic adhesive as compared with the semi-elastic adhesive used above, and 2) heating the laminate during the necking process. For each sample, the non-elastic film layer was stretched to 4×its length prior to lamination to the spunbond layer. The laminates were necked as indicated in Table 5 and tested for permanent set as described above. The non-elastic adhesive used was Rextac® 2730, available from Huntsman Polymers in Odessa, Tex. Further, the samples were heated after necking with heated rolls maintained at a temperature of about 170° F. (76° C.).

A 10 cm×10 cm (3.94 in.×3.94 in.) sample was measured while the laminate was still wound on a roll. Since the materials were wound under tension and some degree of relaxation tends to occur over time, the samples were re-measured after being cut from the roll. Samples C9 and C10 are comparative (baseline) materials wherein the film was stretched but the laminate was not necked.

TABLE 5

| Sample | Laminate Necking Draw | Actual Draw | Adhesive Type | Heat Applied | Sample Size Measured cm (in.) | Sample Size After Relaxation cm (in.) | % Permanent Set cm (in.) |
|---|---|---|---|---|---|---|---|
| C9 | 1.1X | 1.03X | Non-elastic | No | 10 × 10 (3.94 × 3.94) | 10 × 10 (3.94 × 3.94) | — |
| C10 | 1.1X | 1.03X | Semi-elastic | No | 10 × 10 (3.94 × 3.94) | 10 × 10 (3.94 × 3.94) | — |
| 11 | 1.43X | 1.32X | Non-elastic | No | 10 × 10 (3.94 × 3.94) | 10 × 12.2 (3.94 × 4.80) | 76 |
| 12 | 1.4X | 1.28X | Semi-elastic | No | 10 × 10 (3.94 × 3.94) | 9.6 × 11.6 (3.78 × 4.57) | 79 |
| 13 | 1.45X | 1.3X | Semi-elastic | No | 10 × 10 (3.94 × 3.94) | 9.5 × 11.8 (3.74 × 4.65) | 79 |
| 14 | 1.5X | 1.36X | Semi-elastic | Yes | 10 × 10 (3.94 × 3.94) | 10 × 10.5 (3.94 × 4.13) | 78 |
| 15 | 1.45X | 1.3X | Non-elastic | Yes | 10 × 10 (3.94 × 3.94) | 10 × 10.3 (3.94 × 4.06) | 80 |
| 16 | 1.45X | 1.3X | Non-elastic | No | 10 × 10 (3.94 × 3.94) | 10 × 11.25 (3.94 × 4.43) | 80 |

The heat set materials, Samples 14 and 15, maintained their original dimensions better than the materials that were necked and not heat set, based on a comparison between the sample size before and after cutting from the roll. Further, all of the materials, regardless of use of elastic or inelastic adhesive, exhibited a high degree of permanent set. There was little difference between the permanent set of the laminates made with the semi-elastic adhesive and those made with the inelastic adhesive, indicating that the small amount of elastic adhesive used does not bear on the overall extensibility and retractability of the nonwoven web laminate.

The samples were additionally tested for tensile properties in the transverse dimension (TD) and WVTR according to the test methods described above. The results are summarized in Table 6.

Example 3

Laminates were produced generally as described above to determine suitability for use as a liquid transfer material used in, for example, a liner of a diaper or incontinence product. An inelastic nonwoven web layer of 0.58 osy (19.7 gsm) polypropylene spunbond was adhesively laminated to an inelastic nonbreathable film layer of 0.46 osy (15.7 gsm) XP-833 film, available from Huntsman Packaging in Washington, Ga. The XP-833 film layer is a white, 0.6 mil cast embossed, cattalloy-based tri-layered film typically used in personal care products. The layers were attached using an adhesive of H2525A (available from Ato-Findley of Wauwatosa, Wis.) in an amount of 0.09 osy (3 gsm). The thus formed laminate was then drawn 1.45×at a temperature of 190° F. (87.8° C.). To improve the aperturing process conditions, one sample of this necked laminate (Sample 18)

TABLE 6

| Sample | Actual Draw | Adhesive Type | Heat Applied | TD Load at 50% Elongation lb. (kg) | TD Peak Strain % | TD Peak Load lb. (kg) | Unstretched WVTR g/m²/24 hr |
|---|---|---|---|---|---|---|---|
| C9 | 1.03X | Non-elastic | No | 5.73 (2.60) | 62.5 | 6.24 (2.83) | 1667 |
| C10 | 1.03X | Elastic | No | 4.85 (2.20) | 89.7 | 6.15 (2.79) | 2121 |
| 11 | 1.32X | Non-elastic | No | 0.0904 (0.041) | 175 | 4.56 (2.07) | 1272 |
| 12 | 1.28X | Elastic | No | 0.375 (0.170) | 201 | 4.72 (2.14) | 1222 |
| 13 | 1.3X | Elastic | No | 0.617 (0.280) | 212 | 4.78 (2.17) | 903 |
| 14 | 1.36X | Elastic | Yes | 0.419 (0.190) | 192 | 3.57 (1.62) | 1482 |
| 15 | 1.3X | Non-elastic | Yes | 0.375 (0.170) | 174 | 3.37 (1.53) | 1400 |
| 16 | 1.3X | Non-elastic | No | 0.190 (0.086) | 174 | 4.52 (2.05) | N/A |

When the samples were elongated 50%, the control (unnecked) materials, Samples C9 and C10, exhibited a significantly higher load than the necked materials, Sample 11–16, indicating that a much greater force was needed to extend the control samples in the transverse dimension.

was additionally laminated to a 0.77 osy (26 gsm) layer of bonded carded web (BCW) carrier sheet, so that the film layer was disposed between the spunbond and BCW layers, as can be seen in FIG. 17. The BCW carrier sheet was a through air bonded BCW made from a type ESC bicomponent (50% polyethylene/50% polypropylene) 6 denier fiber with an HR6 spin finish, available from Chisso Corporation of Japan, and was treated with a wetting agent. The laminates were then pin-apertured with conically shaped pins having a diameter of about 0.081 in. (0.206 cm). As a comparative example, Sample 19, an untreated spunbond nonwoven web made of polypropylene was also tested. This comparative example represents a typical liner material (which may also be treated with a surfactant) commonly used in diapers and the like. Testing was performed as described above and results indicated in Table 7 below, with the exception that % permanent set was determined from elongations of 63% for Sample 18 and 53% for Sample 17 (which equals approximately ½ of the peak strain). Tensile testing was performed on both of the laminates in the transverse dimension (TD). Additionally, liner runoff testing and one repetition of the diaper runoff test were performed on Sample 18. The results are summarized in Table 7.

TABLE 7

| Sample | Description | Actual Draw | TD Load At 50% Elongation lb. (kg) | TD Peak Strain % | TD Peak Load lb. (kg) | % Permanent Set |
|---|---|---|---|---|---|---|
| C9 | Non-apertured spunbond/film laminate | 1.03X | 5.73 (2.60) | 62.5 | 6.24 (2.83) | NT |
| C10 | Non-aperatured spunbond/film laminate | 1.03X | 4.85 (2.20) | 89.7 | 6.15 (2.79) | NT |
| 17 | Spunbond/film apertured laminate | 1.45X | 4.0 (1.8) | 105 | 7.17 (3.25) | 75.5 |
| 18 | Spunbond/film/ BCW apertured laminate | 1.45X | 5.1 (2.3) | 126 | 10.7 (4.84) | 57.1 |
| C19 | Spunbond (0.4 osy) | N/A | N/A | N/A | N/A | N/A |

NT—Not Tested
N/A—Not Applicable

Table 7 shows that for the samples of the invention, Sample 17 and 18, improvements in TD peak strain were observed over the comparative examples.

Example 4

Laminates were produced generally as described above for Example 3, particularly Samples 18 and 19, with exceptions noted in the table below. Sample 18b is the same as Sample 18 in Table 7 above.

TABLE 8

| Sample | Description | Basis Weight gsm | FIFE Flowback g | Liner Runoff g | Diaper Runoff g |
|---|---|---|---|---|---|
| 18a | Apertured Necked Laminate (non-filled film/0.4 osy polypropylene Spunbond) w/BCW Layer | 68.4 | 0.199 | 12.503 | 0.567 |
| 18b | Spunbond/film/BCW apertured laminate | — | NT | 12.4 | 1.66 |
| C19 | Non-wettable 0.4 osy polypropylene Spunbond | 13.0 | 3.830 | 22.306 | 44.000 |
| C20 | Wettable 0.4 osy polypropylene Spunbond (0.3% Ahcovel) | 13.6 | 5.747 | 0.354 | 0.500 |

TABLE 8-continued

| Sample | Description | Basis Weight gsm | FIFE Flowback g | Liner Runoff g | Diaper Runoff g |
|---|---|---|---|---|---|
| C21 | Non-apertured Necked Laminate (non-filled film/0.4 osy polypropylene Spunbond) w/BCW Layer | 62.4 | 1.256 | 48.673 | 100.000 |

As can be seen from Tables 7 and 8, the liquid transfer materials formed from the apertured necked laminate, Samples 17 and 18, exhibit improved strain over the comparative samples and, at the same time, function simultaneously as a component of a personal care article, e.g. a liner.

Having thus described the invention in detail, it should be apparent that various modifications can be made in the present invention without departing from the spirit and scope of the following claims.

We claim:

1. A liquid transfer material comprising:
   a) at least one first layer of a non-elastic neckable material; and
   b) at least one second layer of a non-elastic film attached to said at least one first layer to form a laminate;
   wherein said laminate is necked in a first dimension and wherein said second film layer has striated rugosities in a dimension perpendicular to said first dimension, and further wherein at least one layer of said laminate is apertured.

2. The liquid transfer material of claim 1, wherein a biasing force applied to said first dimension of said laminate will cause said laminate to extend, and release of the biasing force will cause said laminate to retract.

3. The liquid transfer material of claim 1, wherein said striated rugosities comprise trapezoidal, crenellated, or pleated striations.

4. The liquid transfer material of claim 1, wherein said means of attaching comprises thermal bonding, adhesive bonding, or sonic welding.

5. The liquid transfer material of claim 1, further comprising an additional extensible layer.

6. The liquid transfer material of claim 1, wherein said first dimension is defined by a transverse dimension and said perpendicular dimension is defined by a longitudinal dimension.

7. The liquid transfer material of claim 1, wherein said laminate is breathable.

8. The liquid transfer material of claim 1, wherein said non-elastic neckable material has a basis weight of from about 0.3 osy (10 gsm) to about 2.7 osy (90 gsm).

9. The liquid transfer material of claim 1, wherein said neckable material and said non-elastic film comprises a polyolefin.

10. The liquid transfer material of claim 1 or 9, wherein said neckable material comprises a spunbond nonwoven material.

11. The liquid transfer material of claim 1, wherein said laminate forms at least a portion of a facemask.

12. A conformable liquid transfer material for use as a liner of a personal care absorbent article comprising:
   a) at least one first layer of a non-elastic neckable material; and
   b) at least one second layer of a non-elastic film attached to said at least one first layer to form a laminate, wherein said laminate is necked in a first dimension and wherein said second film layer has striated rugosities in a dimension perpendicular to said first dimension, such that a biasing force applied to said first dimension of said laminate will cause said laminate to extend and conform around the body of the wearer, and further wherein at least one layer of said laminate is apertured.

13. The conformable liquid transfer material of claim 12, wherein said striated rugosities comprise trapezoidal, crenellated, or pleated striations.

14. The conformable liquid transfer material of claim 12, wherein said means of attaching comprises thermal bonding, adhesive bonding, or sonic welding.

15. The conformable liquid transfer material of claim 14, wherein said means of attaching is adhesive bonding.

16. The conformable liquid transfer material of claim 12, wherein said first dimension is defined by a transverse dimension and said perpendicular dimension is defined by a longitudinal dimension.

17. The conformable liquid transfer material of claim 12, wherein said non-elastic neckable material has a basis weight of from about 0.3 osy (10 gsm) to about 2.7 osy (90 gsm).

18. The conformable liquid transfer material of claim 12, wherein said laminate is breathable.

19. The conformable liquid transfer material of claim 12, wherein said neckable material and said non-elastic film comprises a polyolefin.

20. The necked laminate of claim 12 or 19, wherein said neckable material comprises a spunbond nonwoven material.

* * * * *